(12) United States Patent
Plumptre

(10) Patent No.: US 10,034,982 B2
(45) Date of Patent: Jul. 31, 2018

(54) SPINDLE FOR A DRUG DELIVERY DEVICE

(75) Inventor: David Aubrey Plumptre, Worcestershire (GB)

(73) Assignee: Sanofi-Aventis Deutschland GMBH, Frankfurt am Main (DE)

(*) Notice: Subject to any disclaimer, the term of this patent is extended or adjusted under 35 U.S.C. 154(b) by 1230 days.

(21) Appl. No.: 12/788,742

(22) Filed: May 27, 2010

(65) Prior Publication Data

US 2010/0331790 A1    Dec. 30, 2010

Related U.S. Application Data

(60) Provisional application No. 61/182,856, filed on Jun. 1, 2009.

(30) Foreign Application Priority Data

Jul. 10, 2009   (EP) .................................... 09009047

(51) Int. Cl.
*A61M 5/315* (2006.01)
*A61M 5/24* (2006.01)

(52) U.S. Cl.
CPC .... *A61M 5/31511* (2013.01); *A61M 5/31551* (2013.01); *A61M 5/31585* (2013.01); *A61M 5/24* (2013.01); *A61M 5/31541* (2013.01); *A61M 5/31543* (2013.01); *A61M 5/31558* (2013.01); *A61M 5/31575* (2013.01); *A61M 2005/2407* (2013.01); *A61M 2005/2488* (2013.01); *A61M 2005/2492* (2013.01); *A61M 2005/3152* (2013.01); *Y10T 74/19721* (2015.01); *Y10T 74/19953* (2015.01)

(58) Field of Classification Search
CPC .......... A61M 5/31551; A61M 5/31535; A61M 5/31578–5/31586
USPC .......................... 604/134, 135, 155, 207–211
See application file for complete search history.

(56) References Cited

U.S. PATENT DOCUMENTS

| | | | |
|---|---|---|---|
| 533,575 | A | 2/1895 | Wilkens |
| 3,302,462 | A | 2/1967 | Pursell |
| 4,865,591 | A | 9/1989 | Sams |

(Continued)

FOREIGN PATENT DOCUMENTS

| | | |
|---|---|---|
| CA | 2138528 | 12/1998 |
| CA | 2359375 A1 | 7/2000 |

(Continued)

OTHER PUBLICATIONS

Machine Deisgn, Penton Media, vol. 65, No. 11 (1993) p. 36 "Standard Compression Springs Save Space".
Communication—090009047.3 European Search Report.

*Primary Examiner* — Nathan R Price
*Assistant Examiner* — Anh Bui
(74) *Attorney, Agent, or Firm* — Fish & Richardson P.C.

(57) ABSTRACT

A spindle for driving a bung of a cartridge. The spindle includes a generally circular shaft having an outer surface. The generally circular shaft extends from a distal end to a proximal end of said circular shaft. A first helical groove is provided along a first portion of the outer surface. The first helical groove having a first pitch. A second helical groove provided along a second portion of the outer surface of the generally circular shaft. The second helical groove overlapping the first helical groove. The second helical groove having a second pitch.

24 Claims, 19 Drawing Sheets

(56) References Cited

U.S. PATENT DOCUMENTS

| | | | |
|---|---|---|---|
| 5,092,842 A | 3/1992 | Bechtold et al. | |
| 5,226,895 A | 7/1993 | Harris | |
| 5,226,896 A | 7/1993 | Harris | |
| 5,279,586 A | 1/1994 | Balkwill | |
| 5,304,152 A | 4/1994 | Sams | |
| 5,320,609 A | 6/1994 | Haber et al. | |
| 5,378,233 A | 1/1995 | Haber et al. | |
| 5,383,865 A | 1/1995 | Michel | |
| 5,391,157 A | 2/1995 | Harris et al. | |
| 5,423,752 A * | 6/1995 | Haber et al. | 604/86 |
| 5,480,387 A | 1/1996 | Gabriel et al. | |
| 5,505,704 A | 4/1996 | Pawelka et al. | |
| 5,514,097 A | 5/1996 | Knauer | |
| 5,582,598 A | 12/1996 | Chanoch | |
| 5,584,815 A | 12/1996 | Pawelka et al. | |
| 5,591,136 A | 1/1997 | Gabriel | |
| 5,626,566 A | 5/1997 | Petersen et al. | |
| 5,674,204 A | 10/1997 | Chanoch | |
| 5,688,251 A | 11/1997 | Chanoch | |
| 5,792,117 A | 8/1998 | Brown | |
| 5,807,346 A | 9/1998 | Frezza | |
| 5,820,602 A | 10/1998 | Kovelman et al. | |
| 5,851,079 A | 12/1998 | Horstman et al. | |
| 5,921,966 A | 7/1999 | Bendek et al. | |
| 5,957,896 A | 9/1999 | Bendek et al. | |
| 5,961,495 A | 10/1999 | Walters et al. | |
| 6,004,297 A | 12/1999 | Steenfeldt-Jensen et al. | |
| 6,090,080 A | 7/2000 | Jost et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,562,006 B1 | 5/2003 | Hjertman et al. | |
| 6,613,023 B2 | 9/2003 | Kirchhofer et al. | |
| 6,699,224 B2 | 3/2004 | Kirchhofer et al. | |
| 6,899,698 B2 | 5/2005 | Sams | |
| 6,932,794 B2 | 8/2005 | Giambattista et al. | |
| 6,936,032 B1 * | 8/2005 | Bush et al. | 604/187 |
| 7,169,132 B2 | 1/2007 | Bendek et al. | |
| 7,241,278 B2 | 7/2007 | Moller | |
| 7,678,084 B2 | 3/2010 | Judson et al. | |
| 7,850,662 B2 | 12/2010 | Veasey et al. | |
| 8,187,233 B2 | 5/2012 | Harms et al. | |
| 8,353,878 B2 * | 1/2013 | Moller et al. | 604/207 |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0097883 A1 | 5/2004 | Roe | |
| 2004/0127858 A1 * | 7/2004 | Bendek et al. | 604/208 |
| 2004/0162528 A1 | 8/2004 | Horvath et al. | |
| 2004/0186437 A1 | 9/2004 | Frenette et al. | |
| 2004/0210199 A1 | 10/2004 | Atterbury et al. | |
| 2004/0236285 A1 | 11/2004 | Fisher et al. | |
| 2004/0267207 A1 | 12/2004 | Veasey et al. | |
| 2005/0113765 A1 | 5/2005 | Veasey et al. | |
| 2005/0137571 A1 | 6/2005 | Hommann | |
| 2006/0153693 A1 | 7/2006 | Fiechter et al. | |
| 2006/0258988 A1 | 11/2006 | Keitel et al. | |
| 2007/0016143 A1 | 1/2007 | Miller et al. | |
| 2007/0021718 A1 | 1/2007 | Burren et al. | |
| 2008/0027397 A1 | 1/2008 | DeRuntz et al. | |
| 2008/0077095 A1 | 3/2008 | Kirchhofer | |
| 2008/0208123 A1 | 8/2008 | Hommann | |
| 2008/0221530 A1 * | 9/2008 | Glejbol et al. | 604/211 |
| 2009/0227959 A1 * | 9/2009 | Hirschel et al. | 604/207 |
| 2009/0264828 A1 * | 10/2009 | Dette et al. | 604/189 |
| 2009/0275916 A1 | 11/2009 | Harms et al. | |
| 2010/0114025 A1 * | 5/2010 | Moller | A61M 5/20 604/135 |

FOREIGN PATENT DOCUMENTS

| | | |
|---|---|---|
| DE | 93 01 334 U1 | 4/1993 |
| DE | 197 30 999 C1 | 12/1998 |
| DE | 298 18 721 U1 | 3/2000 |
| DE | 10 2005 063 311 A1 | 8/2006 |
| DE | 10 2005 060 928 A1 | 6/2007 |
| DE | 10 2006 038 123 A1 | 2/2008 |
| DE | 10 2007 026 083 A1 | 11/2008 |
| EP | 0496141 A1 | 7/1992 |
| EP | 0 897 728 A1 | 2/1999 |
| EP | 0897729 A2 | 2/1999 |
| EP | 0 937 471 A2 | 8/1999 |
| EP | 0 937 472 A2 | 8/1999 |
| EP | 0937471 | 8/1999 |
| EP | 0937476 | 8/1999 |
| EP | 1 541 185 A1 | 6/2005 |
| EP | 1 776 975 A2 | 4/2007 |
| EP | 1 923 084 A1 | 5/2008 |
| GB | 2 443 390 A | 5/2008 |
| WO | 92/18180 A1 | 10/1992 |
| WO | 93/07922 A1 | 4/1993 |
| WO | 9324160 A1 | 12/1993 |
| WO | 96/23973 A1 | 8/1996 |
| WO | 96/39214 A1 | 12/1996 |
| WO | 97/10864 A1 | 3/1997 |
| WO | 99/03520 A1 | 1/1999 |
| WO | 99/38554 | 8/1999 |
| WO | 01/10484 | 2/2001 |
| WO | 01/19434 A1 | 3/2001 |
| WO | 02/30495 A2 | 4/2002 |
| WO | 02092153 A2 | 11/2002 |
| WO | 03/080160 A1 | 10/2003 |
| WO | 2004/020028 A1 | 3/2004 |
| WO | 2004/064902 A1 | 8/2004 |
| WO | 2004/078241 A1 | 9/2004 |
| WO | 2004/078242 A2 | 9/2004 |
| WO | 2004/078293 A1 | 9/2004 |
| WO | 2005/018721 A1 | 3/2005 |
| WO | 2005/021072 A1 | 3/2005 |
| WO | 2005/044346 A2 | 5/2005 |
| WO | 2005/123159 A2 | 12/2005 |
| WO | 2006/024461 A1 | 3/2006 |
| WO | 2006/058883 A2 | 6/2006 |
| WO | 2006/079481 A1 | 8/2006 |
| WO | 2006/084876 A1 | 8/2006 |
| WO | 2006/089767 A1 | 8/2006 |
| WO | 2006/114395 A1 | 11/2006 |
| WO | 2006/125328 A1 | 11/2006 |
| WO | 2007/017052 A1 | 2/2007 |
| WO | 2007/067889 A1 | 6/2007 |
| WO | 2008/031235 A1 | 3/2008 |
| WO | 2008/074897 A1 | 6/2008 |
| WO | 2008/116766 A1 | 10/2008 |
| WO | 2008/128373 A1 | 10/2008 |

* cited by examiner

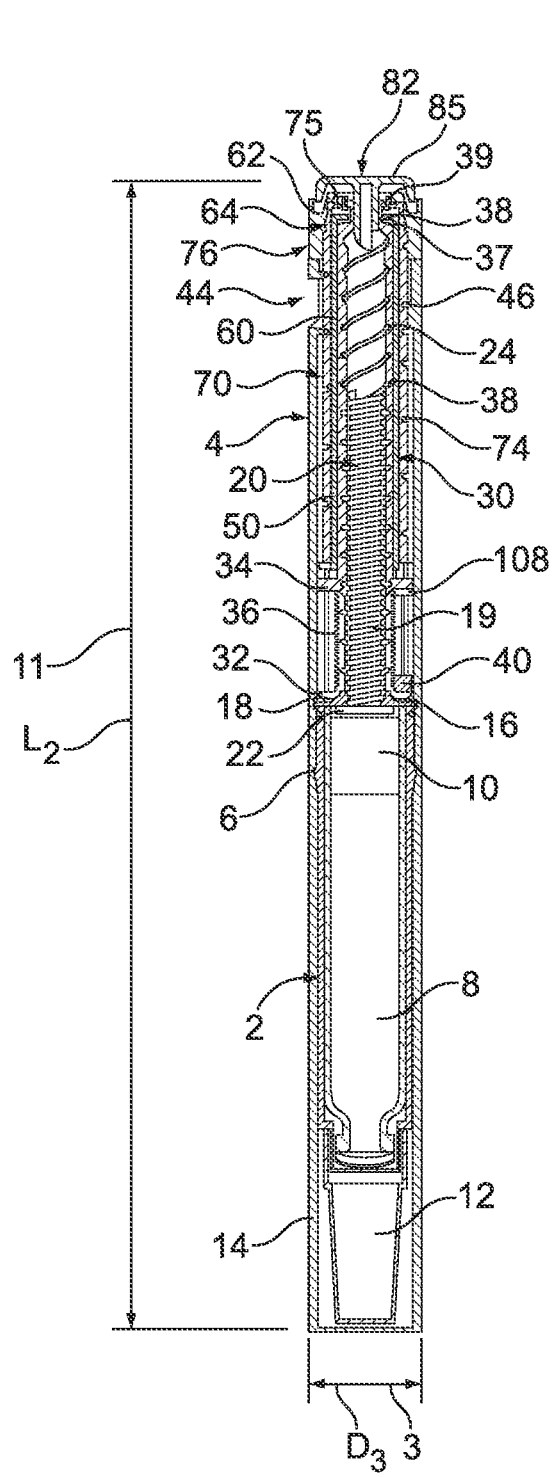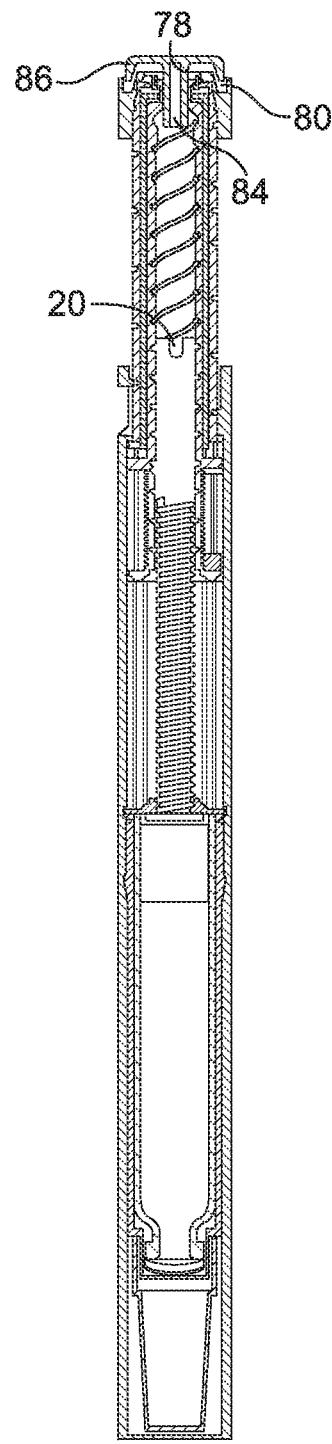
FIG. 1
PRIOR ART
FIG. 2
PRIOR ART

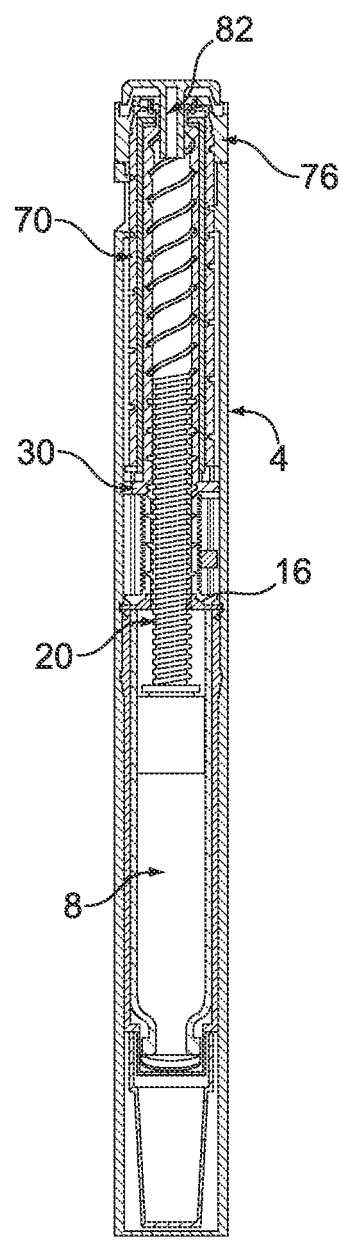
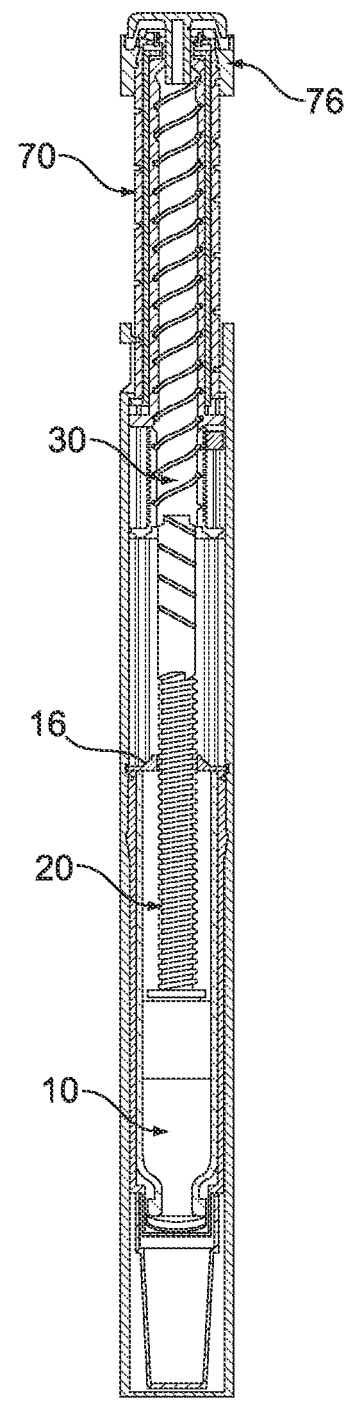
FIG. 3
PRIOR ART
FIG. 4
PRIOR ART

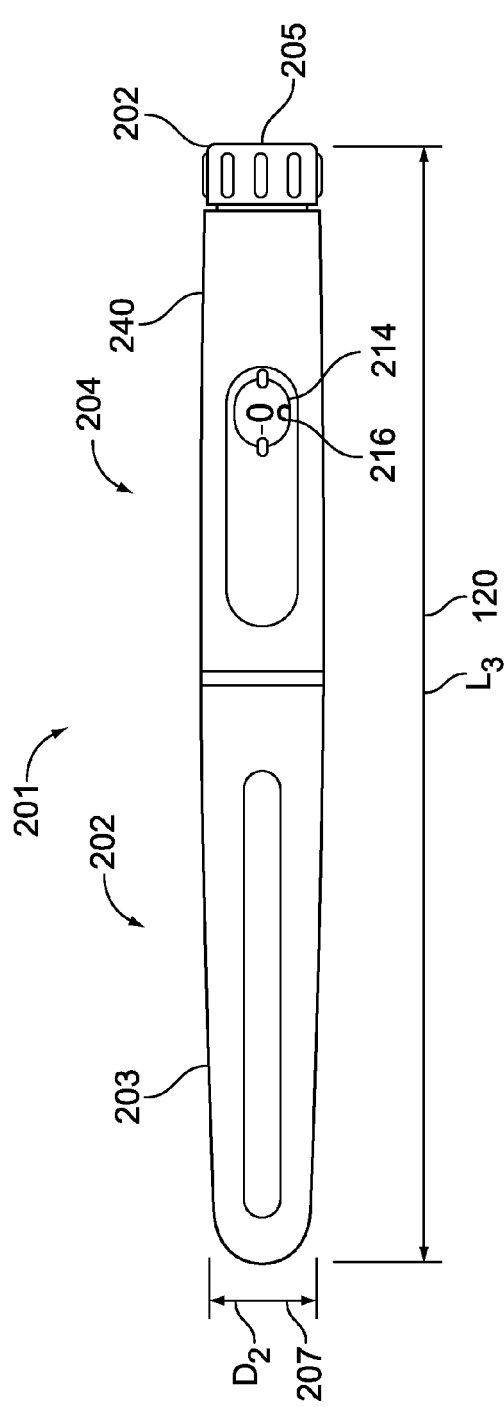
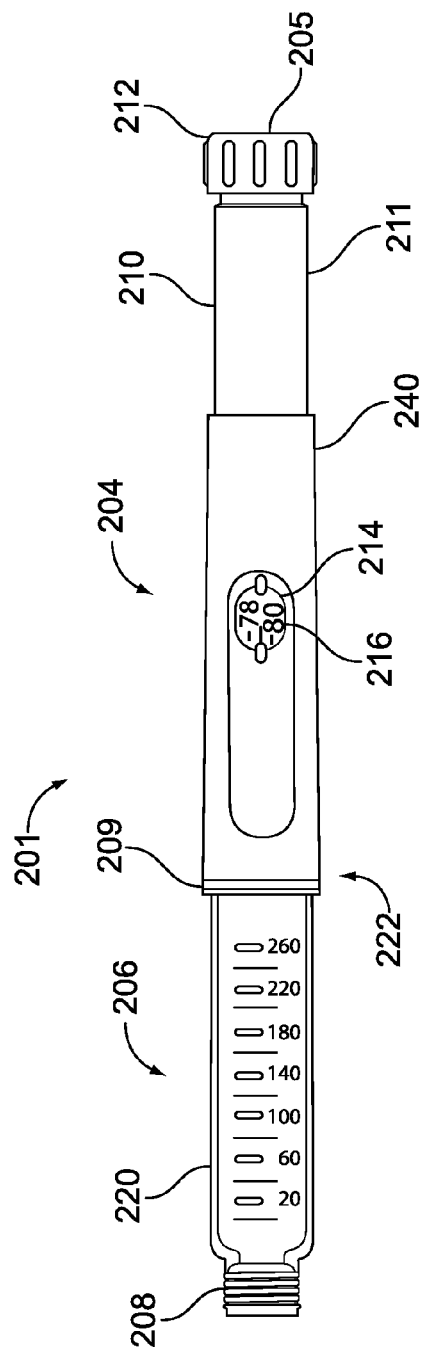
FIG. 14
FIG. 15

SPINDLE FOR A DRUG DELIVERY DEVICE

BACKGROUND

Field of the Present Patent Application

The present patent application is generally directed to a spindle for use with a dose setting mechanism of a drug delivery device. More particularly, the present patent application is generally directed to a spindle for use with drug delivery devices, such as pen type drug delivery devices. Such devices provide for self administration of medicinal product from a multi-dose cartridge and permit a user to set the delivery dose. The present application may find application in both disposable and reusable type drug delivery devices. However, aspects of the invention may be equally applicable in other scenarios as well.

Background

Pen type drug delivery devices have application where regular injection by persons without formal medical training occurs. This is increasingly common among patients having diabetes where self-treatment enables such patients to conduct effective management of their disease.

One such prior art pen type drug delivery device is described in WO 2004/078293 and is illustrated in Applicants' FIGS. 1 through 12. WO 2004/078293 is herein entirely incorporated by reference and to which the reader is directed for any further information and.

As illustrated in FIGS. 1 to 5, there is shown a drug delivery device 1 in a plurality of operating positions: for dose setting and for dose administration or injection. The drug delivery device 1 comprises a housing having a first cartridge retaining part 2, and second main (exterior) housing part 4. A cartridge 8 from which a number of doses of a medicinal product may be dispensed is provided in the cartridge retaining part 2. A piston 10 is retained in a first end of the cartridge. A removable cap 12 is releasably retained over a second end of the cartridge retaining part 2.

An insert 16 is provided at a first end of the main housing 4 and is secured against rotational or longitudinal motion. The insert 16 is provided with a threaded circular opening 18. A first helical groove 19 extends from a first end of a spindle 20. The spindle 20 is generally circular in cross section. The first end of the spindle 20 (a distal end) extends through the threaded opening 18 in the insert 16. A second helical groove 24 extends 15 from a second end of the spindle 20 (a proximal end). In the illustrated arrangement, the second helical groove 24 comprises a series of part helical grooves rather than a complete helical groove.

The first helical groove 19 and the second helical groove 24 are oppositely disposed, i.e., the grooves are of opposite hand. The second end of the spindle 20 (i.e., the proximal end) is provided with a receiving recess 26. A driver 30 extends about the spindle 20 and is provided at a first end with a first radially extending flange 32. A second radially extending flange 34 is provided spaced a distance along the driver 30 from the first flange 32. An intermediate helical groove 36 is provided on an outer part of the driver 30 extending between the first flange 32 and the second flange 34. A helical groove 38 extends along the entire internal surface of the driver 38. The second helical groove 24 (a male helical groove) of the spindle 20 is adapted to work within the helical groove 38.

A shoulder 37 is formed between a second end of the driver 30 (a proximal end of the driver 30) and an extension 38 provided at the second end of the driver 30. The extension 38 has reduced inner and outer diameters in comparison to the remainder of the driver 30. A second end of the extension 38 is provided with a radially outwardly directed flange 39. FIG. 13 illustrates a close up view of the driver 30 and spindle 20 illustrated in FIGS. 1-5.

A clutch 60 is located adjacent the second end of the driver 30. The clutch 60 is generally cylindrical and is provided at a first end (a distal end) with a series of circumferentially directed saw teeth 66 (See, e.g., FIG. 7). Each saw tooth comprises a longitudinally directed surface and an inclined surface. Towards the second end 64 (a proximal end) of the clutch 60 there is located a radially inwardly directed flange 62. The flange 62 of the clutch 60 is disposed between the shoulder 37 of the driver 30 and the radially outwardly directed flange 39 of the extension 38. The second end of the clutch 60 is provided with a plurality of dog teeth 65 (See, e.g., FIG. 8). The clutch 60 is keyed to the drive sleeve 30 by way of splines (not shown) to prevent relative rotation between the clutch 60 and the drive sleeve 30. In one preferred arrangement, the clicker 50 and the clutch 60 each extend approximately half the length of the drive sleeve 30. The clicker 50 and the clutch 60 are engaged as shown in FIGS. 6 and 7, for example.

A dose dial sleeve 70 is provided outside of the clicker 50 and clutch 60 and radially inward of the main housing 4. The dose dial sleeve 70 comprises a distal end 73 and a proximal end 77. A helical groove 74 is provided about an outer surface 72 of the dose dial sleeve 70. The main housing 4 is provided with a window 44 through which a part of an outer surface 72 of the dose dial sleeve 70 may be viewed.

The main housing 4 is further provided with a helical rib 46, adapted to be seated in the helical groove 74 on the outer surface of the dose dial sleeve 70. In one preferred arrangement, the helical rib 46 extends for a single sweep of the inner surface of the main housing 4. A first stop is provided between the splines 42 and the helical rib. A second stop, disposed at an angle of 180" to the first stop, is formed by a frame surrounding the window 44 in the main housing 4.

Returning to FIGS. 1-5, a dose dial grip 76 is disposed about an outer surface of the second end of the dose dial sleeve 70. An outer diameter of the dose dial grip 76 preferably corresponds to the outer diameter of the main housing 4. The dose dial grip 76 is secured to the dose dial sleeve 70 to prevent relative movement between these two components. The dose dial grip 76 is provided with a central opening 78. An annular recess 80 located in the second end of the dose dial grip 76 extends around the opening 78. A button of generally 'T' section is provided at a second end of the device. A stem 84 of the 85 button may extend through the opening 78 in the dose did grip 76, through the inner diameter of the extension 38 of the drive sleeve 30 and into the receiving recess 26 at the proximal end of the spindle 20. The stem 84 is retained for limited axial movement in the drive sleeve 30 and against rotation with respect thereto. A head 85 of the button 82 is generally circular. A skirt 86 extends from a periphery of the head 85. The skirt 86 is adapted to be seated in the annular 10 recess 80 of the dose dial grip 76.

Operation of the drug delivery device is described with reference to FIGS. 9,10 and 11. In FIGS. 9,10 and 11 arrows, A, B, C, D, E, F and G represent the respective movements of the button 82, the dose dial grip 76, the dose dial sleeve 70, the driver 30, 15 the clutch 60, the clicker 50 and the part nut 40 in one arrangement.

To dial a dose in the arrangement illustrated in FIG. 9, a user rotates the dose dial grip 76 (arrow B). With the clicker 50 and clutch 60 engaged, the driver 30, the clicker 50, the clutch 60 and the dose dial sleeve 70 rotate with the dose dial grip 76. Torque is transmitted through the saw teeth 56, 66 between the clicker 50 and the clutch 60. The flexible arm 52 deforms and drags the toothed member 54 over the splines 42 to produce a click. Preferably, the splines 42 are disposed such that each click corresponds to a conventional unit dose, or the like.

The helical groove 74 on the dose dial sleeve 70 and the helical groove 38 in the driver 30 have the same lead. This allows the dose dial sleeve 70 (arrow C) to extend away from the main housing 4 (See, also FIG. 15). In this manner, the driver 30 (arrow D) climbs the spindle 20 at the same rate. At the limit of travel, a radial stop 104 (See, e.g., FIG. 12) on the dose dial sleeve 70 engages either the first stop 100 or the second stop 102 provided on the main housing 4 to prevent further movement. Rotation of the spindle 20 is prevented due to the opposing directions of the overhauled and driven threads on the spindle 20. The part nut 40, keyed to the main housing 4, is advanced along the intermediate thread 36 by the rotation of the drive sleeve 30 (arrow D).

As mentioned above, a first helical groove form 19 extends from a first or distal end of a spindle 20 towards the proximal end. This first helical groove form 19 extends roughly half the length of the spindle 20. The spindle 20 is of generally circular in cross section however other arrangements may also be used. The distal end of the spindle 20 is threadedly extended through the threaded opening 18 in the insert 16. A pressure foot 22 is located at the first end or distal end of the spindle 20 and disposed to abut a second end of the cartridge piston 10.

A second helical groove form 24 extends from a proximal end of the spindle 20. As illustrated, the second helical groove form 24 comprises a series of part male helical grooves rather than a complete helical groove form. The driver 30 comprises an inner helical groove 38 that extends along an internal surface of the driver 30. As illustrated, this inner helical groove 38 extends along the entire internal surface of the driver from the distal to the proximal end of the driver 30. The second male helical groove form 24 of the spindle 20 is adapted to work within this helical groove 38. Although the spindle 20 and the driver 30 arrangement illustrated in FIGS. 1-13 has certain advantages as described and discussed in WO 2004/078293, this spindle and driver arrangement have certain design limitations. For example, the fabrication of the spindle and driver presents certain manufacturing challenges. As described above, this prior art design comprises a spindle 20 comprising two opposite handed groove forms 19, 24. The first groove form 19 is a female groove form and this female groove form mates with the threaded insert 16 of the main outer diameter of the cylindrical form. The second groove form 24 comprises a plurality of male protrusions that engage with the continuous groove 38. This continuous groove 38 is molded along the entire length of the internal surface of the driver 30.

In this prior art drug delivery device, when the driver 30 is rotated relative to the spindle 20 during dose setting, because the driver is coupled to the number sleeve which is threaded to the housing, the driver 30 moves axially. The axial distance moved by the driver 30 will be dependent upon the pitch of the number sleeve groove 74 which is generally similar to the pitch of the continuous internal groove 38 on the driver 30. As such, this prior art spindle 20 and driver 30 arrangement requires that the driver 30 be provided with an internal helical groove 38 over roughly the entire inner surface of the driver 30. In this arrangement, the driver 30 does not disengage from the spindle helical groove 24 during either a dose setting step or during a dose administration step.

This arrangement, therefore, presents certain design and manufacturing challenges. For example, during the molding of driver 30 and in particular, during the process of molding the internal helical groove of driver 30, this step requires that a threaded core pin be spun out of the driver during a de-molding step from the injection mold tooling. This processing step has a disadvantages. For example, Rotating the threaded core pin requires complex gear mechanisms within the molding tool, with flexible water cooling pipes or sealed rotating joints required to enable this rotating core pin to be cooled. Rotating the core extends the cycle time of the tool and generally adds tool complexity and increased maintenance costs.

There is, therefore, a general need to take these issues into consideration in the design and development of a spindle for certain drug delivery devices, such as reusable (i.e., resettable) or disposable (i.e., non-resettable) drug delivery devices.

SUMMARY

According to an exemplary embodiment, a spindle for driving a bung of a cartridge comprises a generally circular shaft having an outer surface. The generally circular shaft extends from a distal end to a proximal end of the circular shaft. A first helical groove is provided along a first portion of the outer surface. The first helical groove having a first pitch. A second helical groove provided along a second portion of the outer surface of the generally circular shaft. The second helical groove overlapping the first helical groove. The second helical groove having a second pitch.

In another arrangement, a dose setting mechanism for use with a drug delivery device is provided. This mechanism comprising a housing and a rotating sleeve in rotatable engagement with respect to the housing. A driver is releasably coupled to the rotating sleeve. A spindle having two overlapping helical grooves is operatively coupled to the driver such that when a user sets a dose by rotating the rotating sleeve, the driver also rotates.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 1 illustrates a sectional view of a first embodiment of the known drug delivery device in a first, cartridge full, position;

FIG. 2 illustrates a sectional view of the drug delivery device of FIG. 1 in a second, maximum first dose dialed, position;

FIG. 3 illustrates a sectional view of the drug delivery device of FIG. 1 in a third, maximum first dose dispensed, position;

FIG. 4 illustrates a sectional view of the drug delivery device of FIG. 1 in a fourth, final dose dialed, position;

FIG. 14 illustrates an arrangement of a drug delivery device;

FIG. 15 illustrates a sectional view of the first arrangement of the drug delivery device illustrated in FIG. 14;

DETAILED DESCRIPTION

Figure 5:
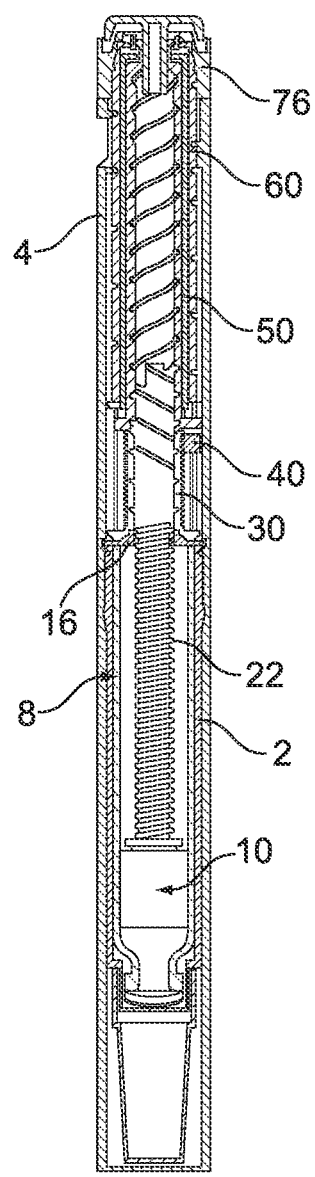
FIG. 5 illustrates a sectional view of the drug delivery device of FIG. 1 in a fifth, final dose dispensed, position.
Figure 6:
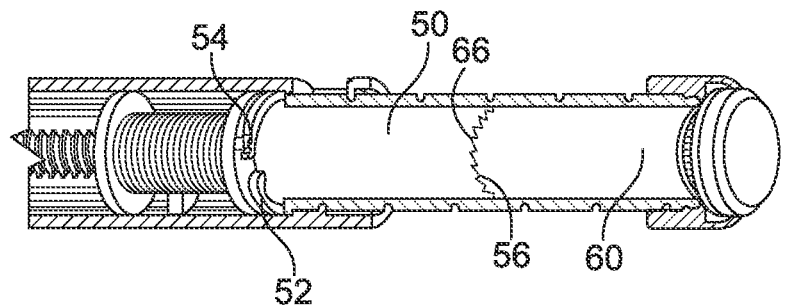
FIG. 6 illustrates a cut-away view of a first detail of the drug delivery device of FIG. 1.
Figure 7:
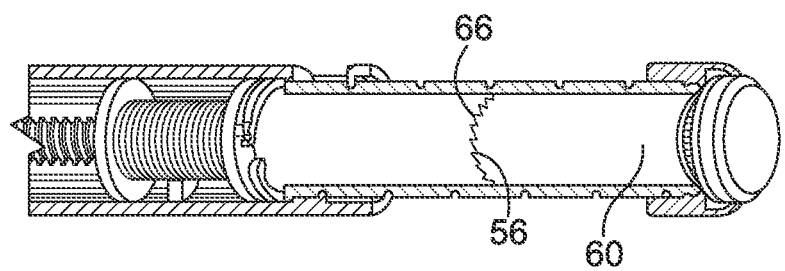
FIG. 7 illustrates a partially cut-away view of a second detail of the drug delivery device of FIG. 1.
Figure 8:
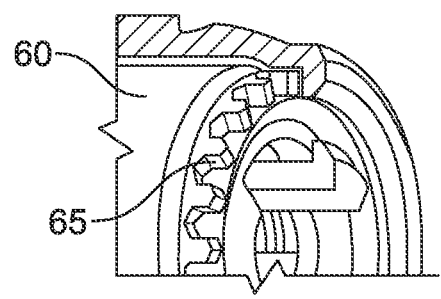
FIG. 8 illustrates a partially cut-away view of a third detail of the drug delivery device of Figure.
Figure 9:
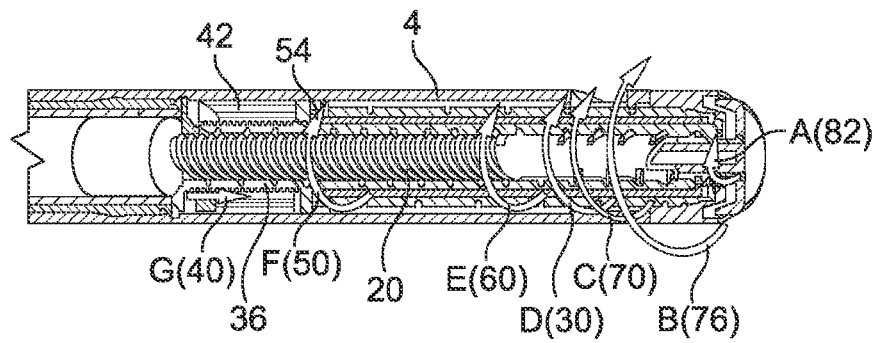
FIG. 9 illustrates a first relative movement of parts of the drug delivery device shown in FIG. 1 during dialing up of a dose.
Figure 10:
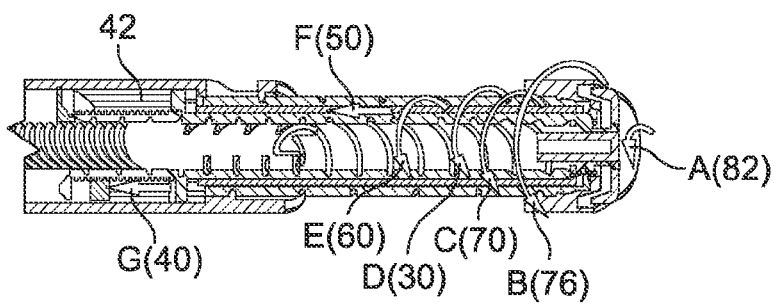
FIG. 10 illustrates the relative movement of parts of the drug delivery device shown in FIG. 9 during dialing down of a dose.
Figure 11:
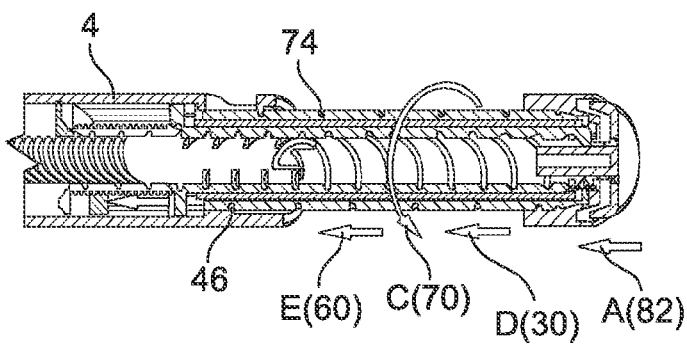
FIG. 11 illustrates the relative movement of parts of the drug delivery device shown in FIG. 9 during dispensing of a dose.
Figure 12:
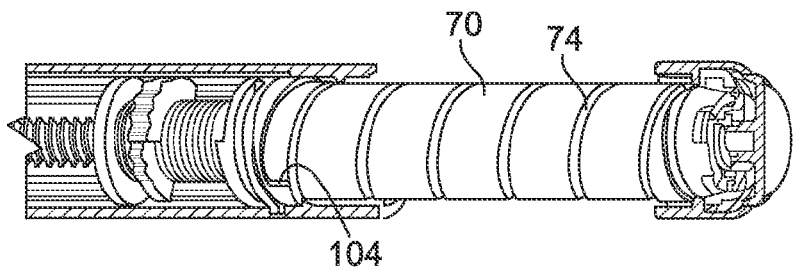
FIG. 12 illustrates a partially cut-away view of the drug delivery device of FIG. 1 in the second, maximum first dose dialed, position.
Figure 13:
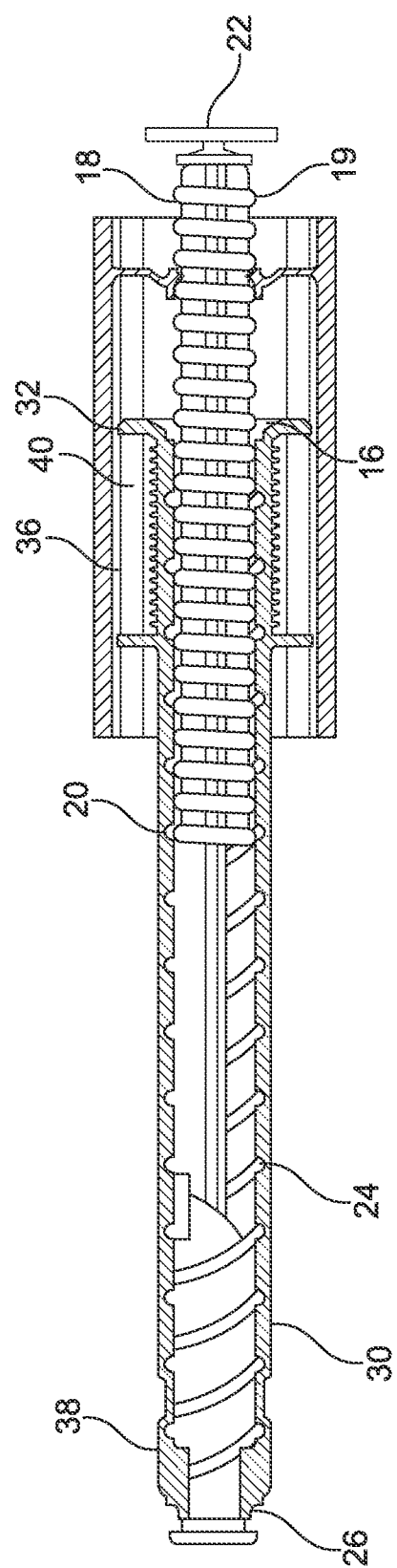
FIG. 13 illustrates a sectional view of the spindle and the driver illustrated in FIGS. 1-2.

Referring to FIG. 14, there is shown a drug delivery device 201 in accordance with a first arrangement of the present invention of Applicants' dual helical spindle and driver configuration. In this arrangement, the drug delivery device 201 may comprise either a resettable or a non-resettable drug delivery device.

The drug delivery device 201 comprises a housing having a first cartridge retaining part 202 and dose setting mechanism 204. A first end of the cartridge retaining means 202 and a second end of the dose setting mechanism 204 are secured together by retaining features. In this illustrated arrangement, the cartridge retaining means 202 is secured within the second end of the dose setting mechanism 204. A removable cap 203 is releasably retained over a second end or distal end of a cartridge retaining part. As will be described in greater detail, the dose setting mechanism 204 comprises a dose dial grip 212 and a window or lens 214. To set a dose of medication contained within the drug delivery device 201, a user rotates the dose dial grip 212 and the window allows a user to view the dialed dose by way of a dose scale arrangement 216.

FIG. 15 illustrates the medical delivery device 201 of FIG. 14 with the cover 203 removed from the distal end of the medical delivery device. As illustrated, a cartridge 220 from which a number of doses of a medicament may be dispensed is provided in the cartridge housing 206. Preferably, the cartridge 220 contains a type of medicament that must be administered often, such as once or more times a day.

One such medicament is insulin. A bung or stopper (not illustrated in FIG. 14) is retained in a first end or a proximal end of the cartridge 220.

As mentioned previously, the dose setting mechanism 204 of the drug delivery device illustrated in FIG. 14 may be utilized as a reusable (and hence resettable) drug delivery device. Alternatively, the dose setting mechanism 204 of the drug delivery device illustrated in FIG. 14 may be utilized as a non-reusable (non-resettable) drug delivery device.

Where the drug delivery device 201 comprises a reusable drug delivery device, the cartridge is removable from the cartridge housing 206. The cartridge 220 may be removed from the device without destroying the device but merely by the user disconnecting the dose setting mechanism 4 from the cartridge holder 220.

In use, once the removable cap 203 is removed, a user can attach a suitable needle assembly to the distal end of the cartridge holder. Such needle unit may be screwed onto a distal end of the housing or alternatively may be snapped onto this distal end. A replaceable cap 203 is used to cover the cartridge holder 206 extending from the dose setting mechanism 204. Preferably, the outer dimensions of the replaceable cap 203 are similar or identical to the outer dimensions of the dose setting mechanism 204 so as to provide an impression of a unitary whole when the replaceable cap 203 is in position covering the cartridge holder 202.

Figure 16:
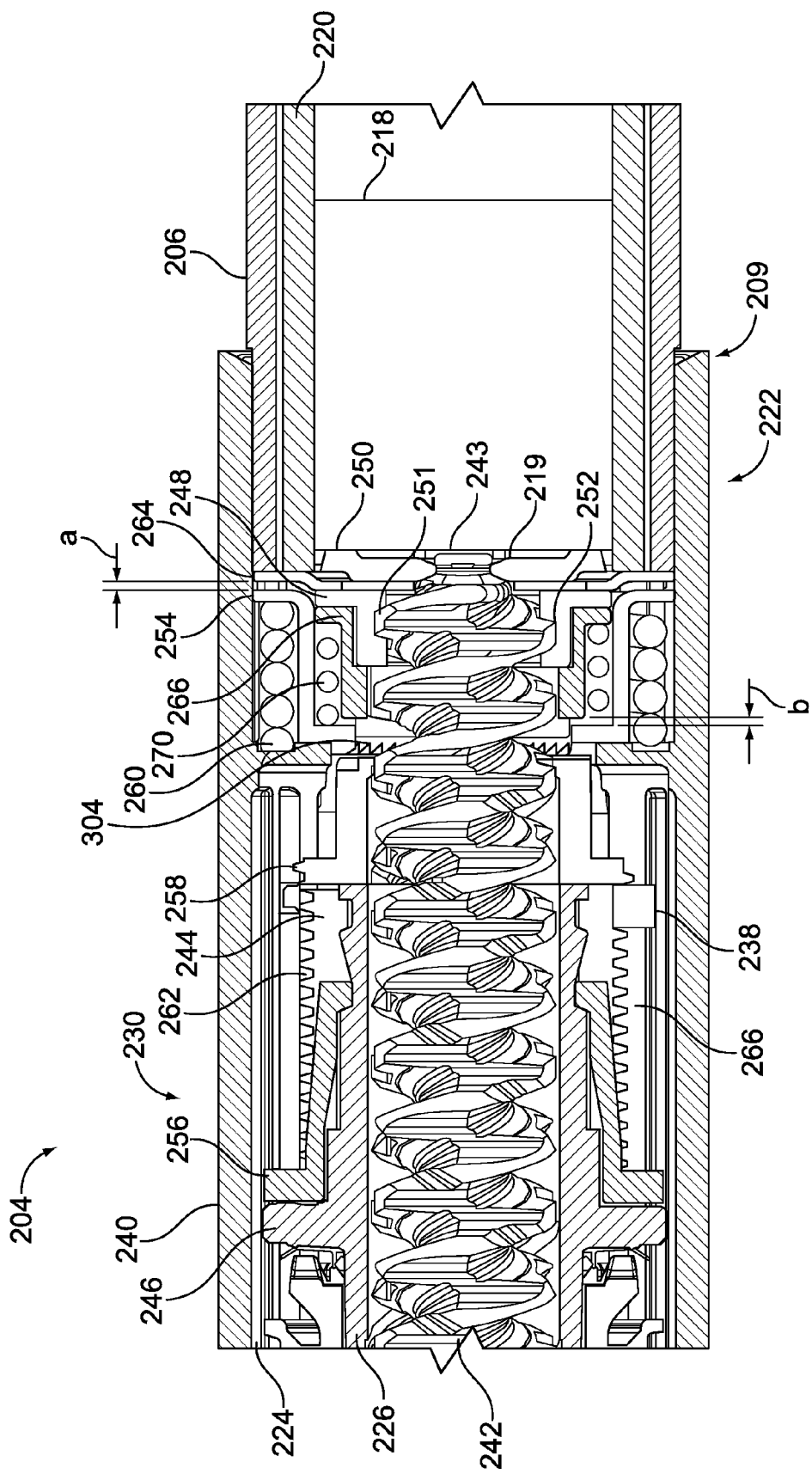
FIG. 16 illustrates a sectional view of the first arrangement of the drug delivery device of FIG. 15 in a first position.

FIG. 16 illustrates a sectional view of the dose setting mechanism 204 removably connected to the cartridge holder 229. The dose setting mechanism 204 comprises an outer housing 240 containing a spindle 242, a number sleeve 224, a clutch 226, and a driver 230. As will be described in greater detail below, the spindle comprises a first groove 219 and a second groove 221 that preferably overlaps with the first groove 219. The first helical groove 219 extends from a first end of a spindle 242. In one arrangement, the spindle 242 is of generally circular shape however other arrangements may also be used. The first end of the spindle 242 (a distal end 243) extends through a pressure plate 264. A spindle bearing 250 is located at the distal end 243 of the spindle 242. The spindle bearing 250 is disposed to abut a second end of the cartridge piston 218. The driver 230 extends about the spindle 242.

The clutch 226 is disposed about the driver 230, between the driver 230 and a number sleeve 224. The clutch 226 is located adjacent the second end of the driver 230. A number sleeve 224 is provided outside of the clutch 226 and radially inward of the housing 240. The main housing 204 is provided with a window 214 through which a part of an outer surface 211 of the number sleeve 224/210 may be viewed. Returning to FIGS. 14-15, a dose dial grip 212 is disposed about an outer surface of the second end of the number sleeve 210. An outer diameter of the dose dial grip 212 preferably corresponds to the outer diameter of the housing 240. The dose dial grip 212 is secured to the number sleeve 210 to prevent relative movement between these two components. In one preferred arrangement, the dose dial grip 212 and button 25 comprise a one piece component that is rotationally coupled to a clutch and drive sleeve and axially coupled to the number sleeve 210. However, alternative coupling arrangements may also be used.

Figure 17:
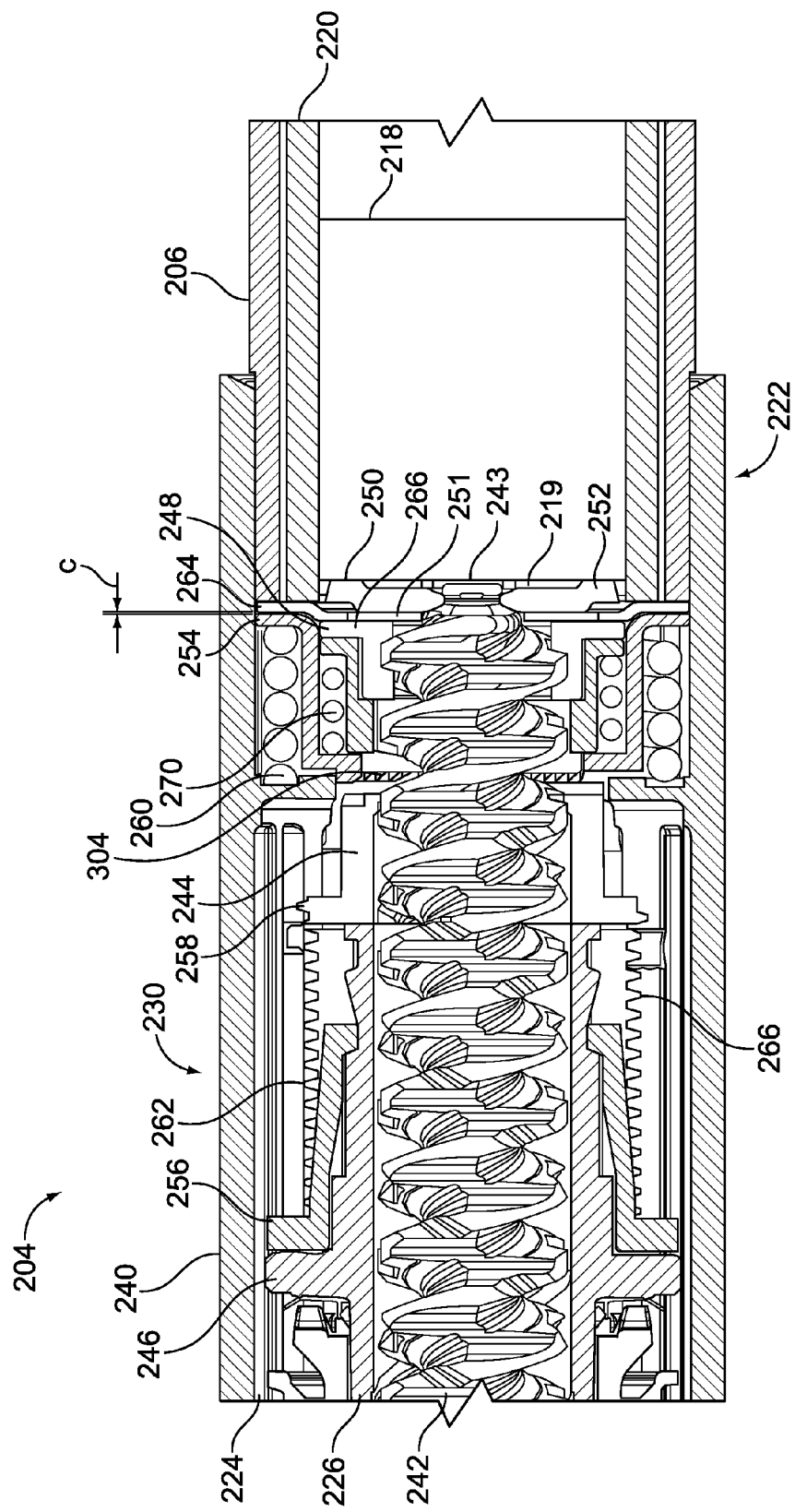
FIG. 17 illustrates a sectional view of the first arrangement of the drug delivery device of FIG. 15 in a second position.
Figure 18:
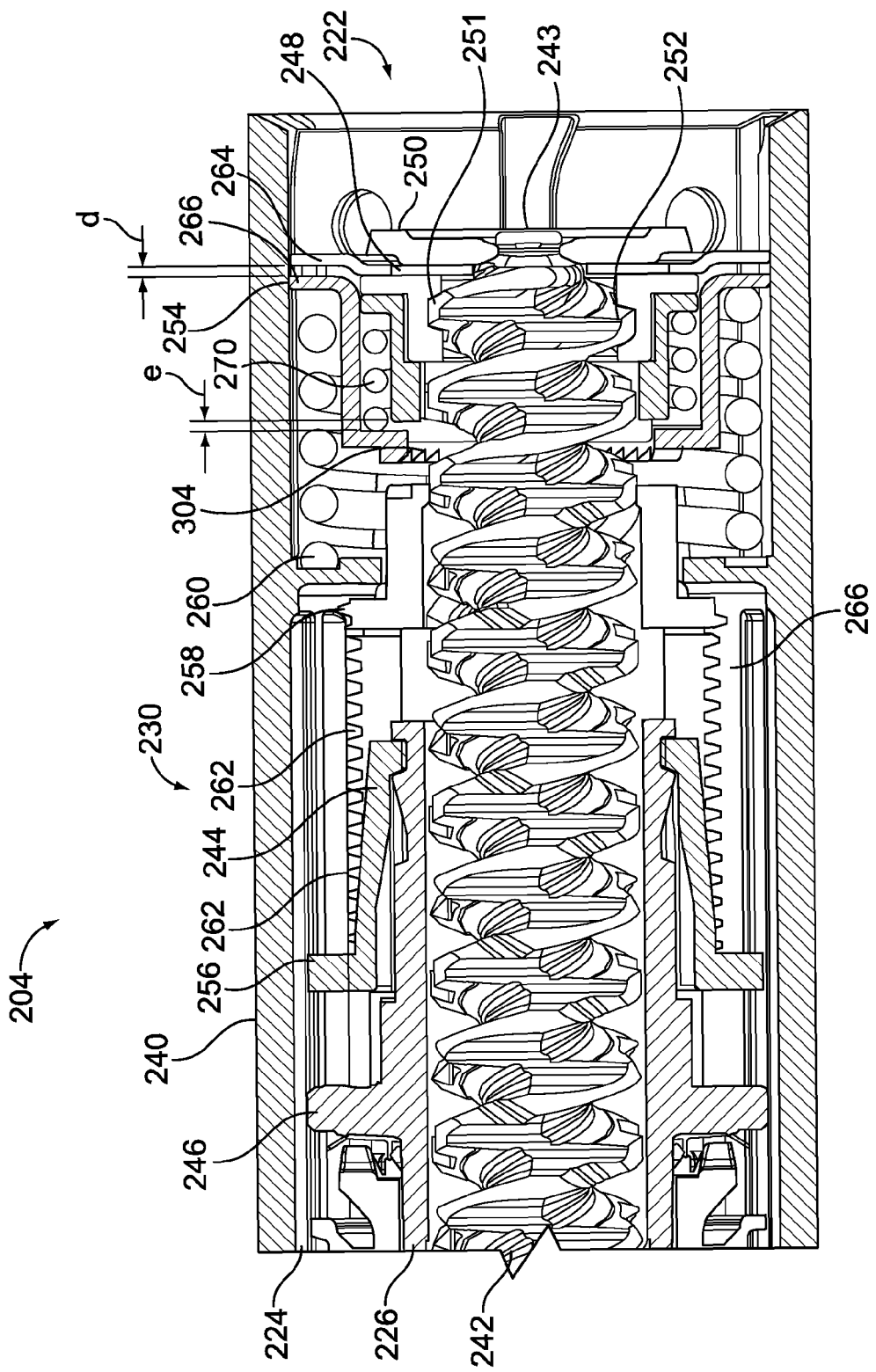
FIG. 18 illustrates a sectional view of the first arrangement of the drug delivery device of FIG. 15 in a third position.

As illustrated in FIGS. 16-18, in this arrangement, driver 230 comprises a first driver portion 244 and a second driver portion 246 and these portions extend about the spindle 242. Both the first and the second driver portions 244, 246 are generally cylindrical. As can be seen from FIG. 19, the first driver portion 244 is provided at a first end with a first radially extending flange 256. A second radially extending flange 258 is provided spaced a distance along the first driver portion 244 from the first flange 256. An intermediate helical groove 262 is provided on an outer part of the first driver portion 244 extending between the first flange 256 and the second flange 258. A portion or a part helical groove 268 extends along an internal surface of the first driver portion 244. One of the overlapping grooves 219, 221 of the spindle 242 is adapted to work within this part helical groove 268.

A dose limiter 238 (illustrated in FIG. 16) is located between the driver 230 and the housing 204, disposed between the first flange 256 and the second flange 258. In the illustrated arrangement, the dose limiter 238 comprises a nut. The dose limiter 238 has an internal helical groove matching the helical groove 266 of the driver 230. In one preferred arrangement, the outer surface of the dose limiter 238 and an internal surface of the housing 240 are keyed together by way of splines. This prevents relative rotation between the dose limiter 238 and the housing 240 while allowing relative longitudinal movement between these two components.

Referring back to FIGS. 15-18, essentially, in normal use, the operation of the dose setting mechanism 204 occurs as follows. To dial a dose in the arrangement illustrated in FIGS. 14-18, a user rotates the dose dial grip 212. The driver 230, the clutch 226 and the number sleeve 210 rotate along with the dose dial grip 212.

The number sleeve 210 extends in a proximal direction away from the housing 240. In this manner, the driver 230 essentially climbs one of the grooves 219, 221 provided along the surface of the spindle 242. At the limit of travel, a radial stop on the number sleeve 210 engages either a first stop or a second stop provided on the housing 240 to prevent further movement. Rotation of the spindle 242 is prevented due to the opposing directions of the overhauled and driven threads on the spindle 242. The dose limiter 238, which in this arrangement is keyed to the housing 240, is advanced along the thread 266 by the rotation of the driver 230. Other dose limiter 238 configurations may also be used.

FIG. 15 illustrates a preferred arrangement of Applicants' medical delivery device after a desired dose has been dialed. In this illustration, a desired dose of 79 International Units ("IU") has been dialed. When this desired dose has been dialed, the user may then dispense the desired dose of 79 IU by depressing the dial grip 212. As the user depresses the dial grip 212, this displaces the clutch 226 axially with respect to the number sleeve 210, causing the clutch 226 to disengage from the number sleeve 210. However the clutch 226 remains keyed in rotation to the driver 230. The number sleeve 210 is now free to rotate.

In this illustrated arrangement, the driver 230 is prevented from rotating with respect to the main housing 204. However, the driver 230 is free to move axially with respect to the main housing 204. The longitudinal axial movement of the driver 230 causes the spindle 242 to rotate and thereby to advance the piston 218 in the cartridge 220 in the distal direction.

In normal use, the first and second portions 244, 246 of the driver 230 are coupled together when the dose dial sleeve 210 is rotated. That is, in normal use, the first and second portions 244, 246 of the driver 230 are coupled together with the dose dial sleeve 210 when a user sets a dose by turning the dose dial grip 212. After each dispensed dose, the spindle 242 is pushed in a distal direction, acting on the bung 218 of the cartridge 220 to continue to expel a dialed dose of medication out of an attached needle assembly releasably connected to the distal end 208 of the cartridge holder 206.

After a user uses the drug delivery device 201 to dispense all of the medication contained in the cartridge 220, the user may wish to replace the empty cartridge in the cartridge holder 206 with a new cartridge. The user must then also reset the dose setting mechanism 204: for example, the user must then retract or push the spindle 242 back into the dose setting mechanism 204.

If the user decides to replace an empty cartridge and reset the device 201, the first and second driver portions 244, 246 must be de-coupled from one another. After decoupling the first driver portion 244 from the second driver portion 246, the first driver portion 244 will be free to rotate while the second driver portion 246 will not be free to rotate.

Figure 20:
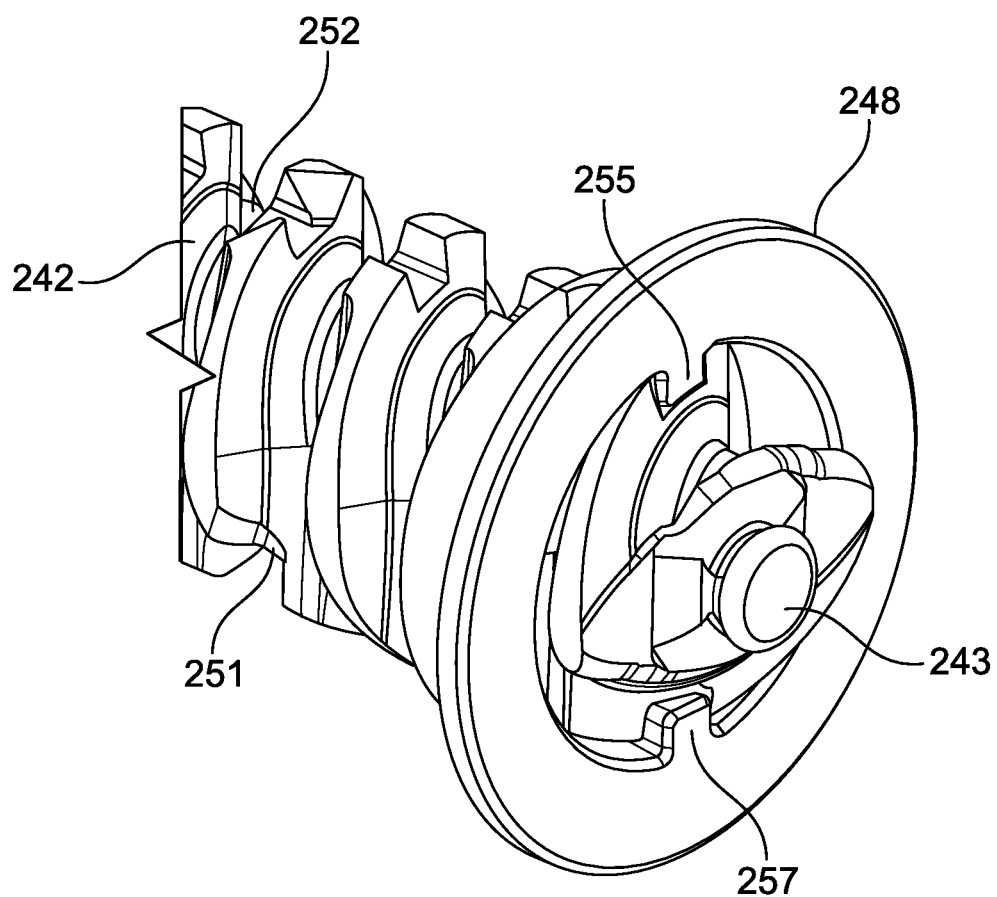
FIG. 20 illustrates a distal end of the spindle of the dose setting mechanism illustrated in FIGS. 15-18.

During a device resetting step, rotating the first driver portion 244 achieves at least two results. First, rotation of the first driver portion 244 will reset the axial position of the spindle 42 with respect to the dose setting mechanism 204 since rotation of the first driver portion 244 causes the spindle 242 to rotate. Rotation of the spindle 242 (because the spindle is threadedly engaged with the nut 266) causes it to move in a proximal direction back into the dose setting mechanism. In addition, FIG. 20 illustrates an arrangement for connecting the spindle 242 to a spindle guide 248. In FIG. 20, the spindle 242 comprises a first 251 spline and a second spline 252. The spindle guide 248 comprises an essentially circular member having an aperture. The aperture includes two inner protruding members 255, 257 that engage the first and second splines 251, 252 respectively, so that the spindle guide 248 locks onto the spindle and rotates along with the spindle during spindle rotation.

Rotation of the first driver portion 244 will also axial move or reset a dose limiter 238 to an initial or start position. That is, as the first driver portion 244 is rotated back to an initial start position, because the dose limiter 238 is threadedly engaged to the outer groove and splined to an inner surface of a housing portion, such as the outer housing 240. In this configuration, the dose limiter 238 is prevented from rotating but will move along the outer groove 262 of the first driver portion 244 as this portion is rotated during a resetting step.

Referring to a first driver arrangement illustrated in FIG. 16, the two portions of the driver 230 are decoupled when the first driver portion 244 is pulled axially away from the second driver portion 246. This may be achieved by the use of a biasing means (such as at least one spring) that interacts together when the cartridge holder 206 is removed from the front or distal end of the device to first lock the relative rotation between the spindle 242 and a spindle guide 248 through which the spindle passes, and then to push this spindle guide 248 and also nut 266 axially a fixed distance. Because the spindle 242 is rotationally locked to this spindle guide 248 and is threadedly engaged with the spindle nut 266, the spindle 242 will move axially.

The spindle 242 may be coupled via a groove engaged to the first driver portion 244. The first driver portion 244 is prevented from rotation by a clutched connection to the second driver portion 246. In one preferred arrangement, the second driver portion 246 is prevented from rotation by a clicker detent 75. The clicker detent 75 resides between the clutch and the flange 280 on the driver 246. Therefore, axial movement of the spindle 242 decouples the two driver portions 244, 246 so that the clutched connection becomes de-coupled.

This sequence of operation as the cartridge holder 206 is removed or disconnected from the dose setting mechanism 204 is illustrated in FIGS. 16-18. In FIG. 16, the various component parts of the drug delivery device include: a dose setting housing 240, a cartridge 220, a spindle 242, first driver portion 244; second driver portion 246, spindle bearing 250, spindle guide 248; 256 spring plate 254; a main spring 260, a pressure plate 264, a cartridge holder 220; a spindle nut 266; and a second spring 270. In this preferred arrangement, the spindle guide 248 is rotationally fixed relative to the spindle 220. In addition, the 256 spring plate 254, pressure plate 64 and spindle nut 266 are rotationally fixed relative to the outer housing.

In FIG. 16, the cartridge holder 206 is fitted via apertures in the pressure plate 264 and applies a load to the spring plate 254. This compresses the first biasing means or main spring 260. These apertures in the pressure plate 264 (not shown) allow the pressure plate 64 to move away from the spring plate 254 (in a distal direction towards the cartridge holder 206) under the action of the second biasing means or second spring 270. This will open up a Gap "A" as shown in FIG. 16. Gap "A" is a gap created between the pressure plate 264 and the spring plate 254. This will also open Gap "B", a gap between the spindle nut 266 and the spring plate 254. This Gap B is illustrated in FIG. 16. The Gap B in conjunction with the light force from the second spring or biasing means 270 moves the spindle nut 266 towards the distal end of the drug delivery device 201. This applies light pressure to the spindle guide 248.

The spindle guide 248 is compressed under the action of the second spring 270 between the spindle nut 266 and pressure plate 264. This light force coupled with the friction coefficient on either side of a flange of the spindle guide 248 through which this force acts, provides a resistance to rotation of the spindle guide 248 and therefore a resistance to rotation of spindle 242 as well. One advantage of this configuration is that at the end of a dose, it is advantageous to prevent the spindle 242 from back-winding into the dose setting mechanism 204 under light residual loads that may remain from the cartridge bung 218. By preventing the spindle 242 from back-winding in a proximal direction, a distal end 243 of the spindle 242 (and hence the spindle bearing 250) remains on the bung 218. Maintaining the distal end 243 of the spindle 242 on the bung 218 helps to prevent a user from administrating a potential under-dose.

When the user delivers a dose, as the dispense force increases, the rearward load on the spindle nut 266 increases to a point at which the spindle nut 266 travels back in a proximal direction and compresses the second spring 270. This releases the axial force acting on the spindle guide 248. This removes the resistance to rotation of the spindle guide 248 and hence spindle 242. This configuration therefore prevents back-winding of the spindle 242 under low loads caused by the cartridge bung 218 but does not add to the dispense force once this dispense force has increased above a certain threshold level.

FIG. 17 illustrates the dose setting mechanism 204 of FIG. 16 with the cartridge holder 206 rotated to release a connection type between the housing 240 of dose setting mechanism 204 and the cartridge holder 206. In one arrangement, this connection type 222 is a bayonet type connection. However, those of ordinary skill in the art will recognize that other connection types 222 may be used as well such as threads, snap locks, snap fits, luer locks and other similar connection types. In the arrangement illustrated in FIGS. 16-18, by rotating the cartridge holder 206 with respect to housing 240, features that were initially acting on the spring plate 254 to compress the main biasing means 260 through apertures in the pressure plate 264, rotate so that they now release this force created by the main biasing means 260. This allows the spring plate 254 to move in a distal direction until the spring plate 254 contacts the spindle nut 266 on an inside face of the spindle nut 266.

In this second condition, the previous discussed Gap "A" (from FIG. 16) has now been reduced to a Gap "C" (as seen in FIG. 17). In this manner, the relative high axial force from the main biasing means 260 acts through the spring plate 254 to the spindle nut 266 and from the spindle nut 266 through the spindle guide 248 to the pressure plate 264. This relative high axial force from the main biasing means 260 is sufficient to prevent the spindle guide 248, and hence spindle 242, from rotating. After sufficient rotation of the cartridge holder 206, the cartridge holder 206 disengages from the connection type 222 with the housing 240. The cartridge holder 206 is then driven in an axial direction away from the housing 240 by the main biasing means 260 (i.e., in a distal direction). However, during this movement, the main spring 260 continues to load the cartridge holder 206 through the spindle guide 248 and therefore the spindle 242 is prevented from rotation. As the spindle 242 is also threaded to the first driver portion 244, the first driver portion 244 is also pulled axially in a distal direction and in this manner becomes disengaged from the second driver portion 246. The second driver portion 246 is axially fixed and is prevented from rotation. In one arrangement, the second driver portion 246 is prevented from rotation by clicker elements and prevented from axial movement by its axial coupling to the number sleeve.

FIG. 18 illustrates the dose setting mechanism illustrated in FIG. 16 in a third position, that is, with the cartridge holder 206 removed. As the cartridge holder 206 is removed from the housing 240, the bayonet features shown in FIG. 18, (illustrated as round pegs extending radially inwards on inside of inner housing) limit travel of the pressure plate 264 but allows Gap "C" (as shown in FIG. 17) to increase to a wider Gap "D" (as shown in FIG. 18). As a result, Gap "E" develops. Gap "E" removes the high spring force created by the main biasing means 260 from the spindle guide 248. The dose setting mechanism 204 in FIG. 17 is now ready to be reset.

To reset this dose setting mechanism 204, a user retracts the spindle 242 in a proximal direction back into the housing 240 by pushing on the distal end 243 of the spindle 242. Therefore, during this re-setting step of the dose setting mechanism 204, as the spindle 242 is pushed back into the dose setting mechanism 204, the movement of the spindle 242 causes the spindle nut 266 to move back against a light spring force created by the second biasing means 270. This movement releases the axial load and hence resistance to rotation from the spindle guide 248. Therefore, as the dose setting mechanism 204 is reset by the spindle 242 rotating back into the dose setting mechanism 204, the spindle guide 248 also rotates.

As the spindle 242 is pushed back further into the dose setting mechanism 204, the spindle 242 rotates through the spindle nut 266 by way of one of the helical grooves provided along the surface of the spindle 242. As the first driver portion 244 is de-coupled from the second driver portion 246, the first driver portion 244 rotates (with the flexible elements 302, 303 running on a conical surface groove 290 formed by the first annular ring 291 on the second half of the drive sleeve 246, FIGS. 16 and 17). This accommodates the axial and rotational movement of the spindle 242.

As the first driver portion 244 rotates during reset, first driver portion 244 also re-sets the dose nut. More specifically, as the first driver portion 244 rotates, the dose nut which is not rotatable since it is splined to an inner surface of the housing 240, traverses along the helical groove 262 provided along an outer surface of the first driver portion 244 and traverses back to an initial or starting position. In one preferred arrangement, this starting position of the dose nut resides along the first radial 256 flange of the first driver portion 244.

After the dose setting mechanism 204 has been reset, the dose setting mechanism 204 must be re-connected to the cartridge holder 206. When re-connecting these two components, the process generally works in reverse. However, this time the axial compression of the main spring 260 causes the first driver portion 244 to re-engage with the second driver portion 246. In this manner, the flexible elements re-engage with the second annular ring 294 on the second driver portion 246.

Figure 19:
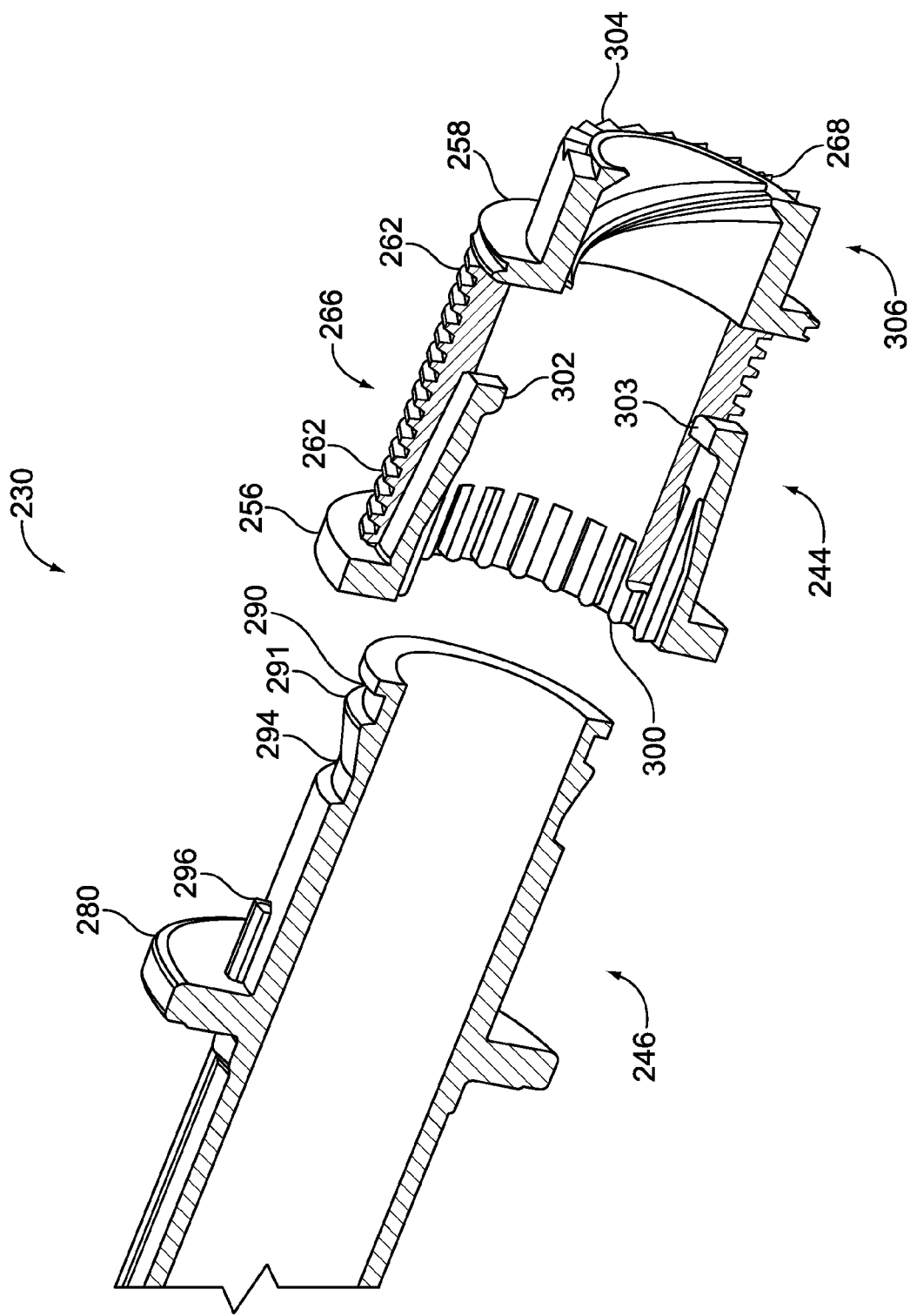
FIG. 19 illustrates a first arrangement of the driver illustrated in FIGS. 15-18 comprising a first driver portion and a second driver portion.

FIG. 19 illustrates a first arrangement of the second driver portion 246 and the first driver portion 244 illustrated in FIG. 16. As shown in FIG. 19, second driver portion 246 is generally tubular in shape and comprises a first annular groove 290 at a distal end of the second driver portion 246. The first annular groove 290 comprises a conical face 291. The second driver portion further comprises a second annular groove 294 and at least one spline 296 positioned along a surface of the second driver portion.

The first driver portion 244 is also generally tubular in shape and comprises a first and a second flexible element 302, 303 and a plurality of spline recesses 300. The plurality of recesses 300 releasably connect the longitudinal spline 296 of the first driver portion 244 to second driver portion 246 when both first and second driver portions 244, 246 are pushed axially together so that they releasably engage one another. When pushed together, the flexible elements 302, 303 of the first driver portion 244 are pushed over the first annular groove 290 of the second driver portion 246 and then stop when the flange 280 of the second driver portion abuts the first axial flange 256 of the first driver portion 244.

The first driver portion 244 also includes a plurality of ratchet features 304. These ratchet features 304 are provided at a distal end 306 of the first driver portion 244. These ratchet features 304 engage similar ratchet features on the spring plate 225 which are splined to the housing 202. (See e.g., FIGS. 16-18) At the end of the re-setting step, these ratchet features engage one another so as to prevent the first driver portion 244 from rotating, thereby ensuring that as the spindle 242 is reset further, the first drive portion moves axially to re-engage the second drive portion 246 rather than rotate on the conical face 290. These features also orientate the spring plate 225 relative to the second driver portion 244 so that the two driver portions 244, 246 engage easily during assembly or after reset. Therefore, these ratchet features also prevent the coupling features 300, 296 from clashing with one another.

The first driver portion 244 also includes a helical member 268. This helical member, preferably a partial helical member comprises less than one turn of a helix, engages a helical groove provided along the spindle 242. By way of this engagement, during a dose setting step, the driver portion 244 can be rotated while the spindle does not rotate during this step.

Figure 21:
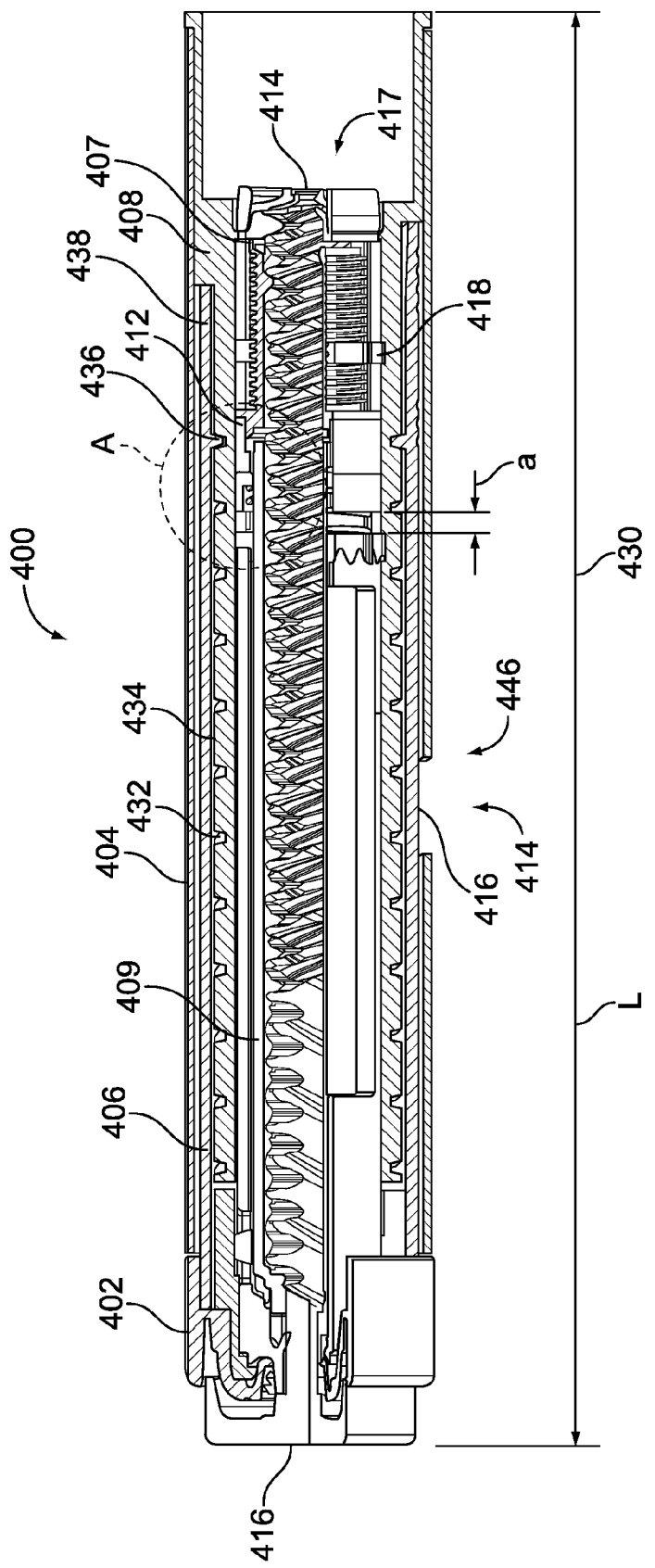
FIG. 21 illustrates a sectional view of a second arrangement of a dose setting mechanism of the drug delivery device illustrated in FIG. 14.
Figure 22:
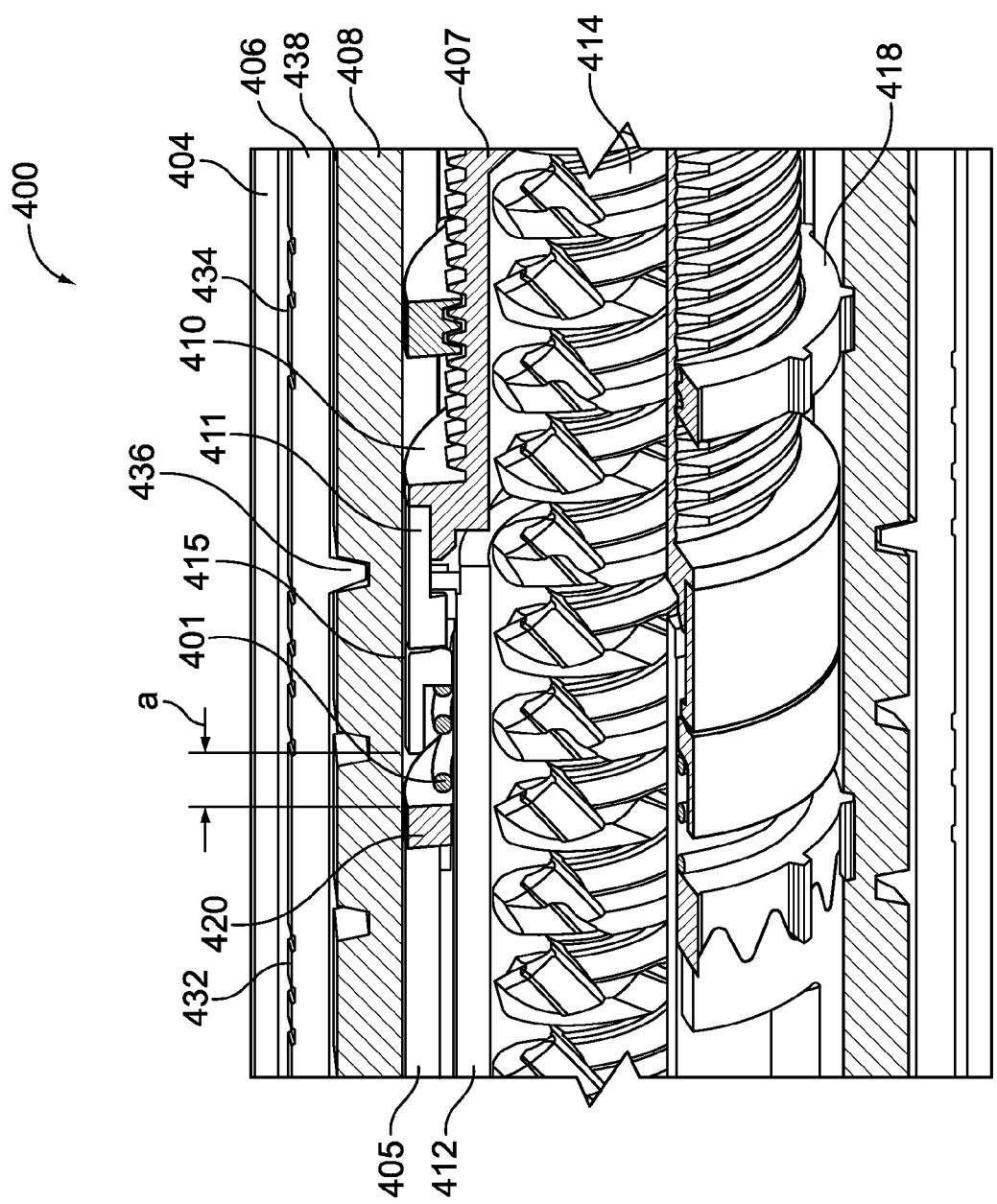
FIG. 22 illustrates a partial sectional view of the second embodiment of the dose setting mechanism illustrated in FIG. 21.
Figure 23:
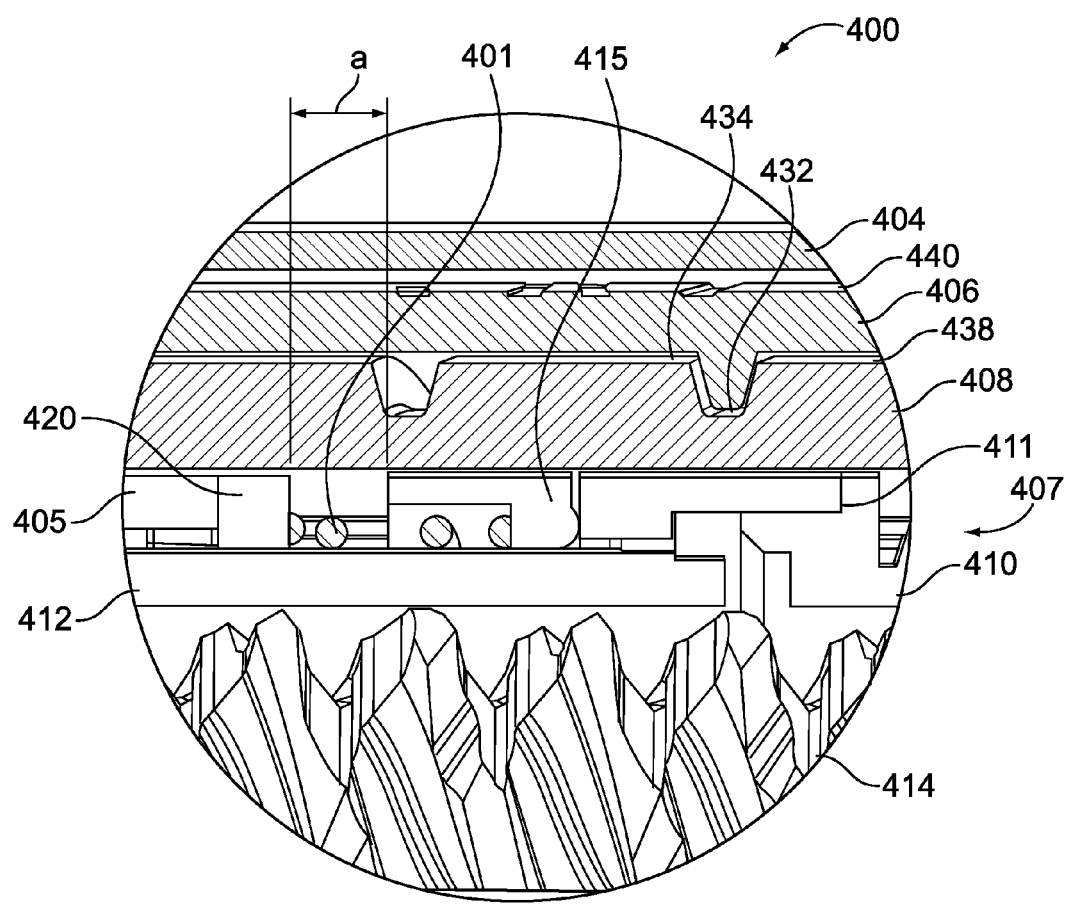
FIG. 23 illustrates a close up view of Gap A illustrated in FIG. 21.

A second arrangement of resettable dose setting mechanism is illustrated in FIGS. 21-23. FIG. 21 illustrates a section view of a second arrangement of a dose setting mechanism 400. Those of skill in the art will recognize that dose setting mechanism 400 may include a connection mechanism for releasably connecting to a cartridge holder, like the cartridge holder 206 illustrated in FIG. 15. FIG. 22 illustrates a portion of the dose setting mechanism illustrating the driver operation. FIG. 23 illustrates a close up view of the coupling between the first driver portion and the second driver portion illustrated in FIG. 22. The second arrangement of the dose setting mechanism 400 operates in a similar fashion to the first arrangement of the dose setting mechanism 204 illustrated in FIGS. 14-15.

With reference to FIGS. 21-23, the dose setting mechanism 400 comprises a dose dial grip 402, a spring 401, a housing 404, a clutch 405, a number sleeve 406, and an inner housing 408. Similar to the driver 230 illustrated in FIGS. 15-18, driver 409 of dose setting mechanism comprises a first driver portion 407 and a second driver portion 412. In one arrangement, the first driver portion 407 comprises a first component part 410 and a second component part 411. Alternatively, the first driver portion 407 is an integral component part.

As illustrated in FIGS. 21 and 22, the driver 409 is de-coupled from the dose setting mechanism 400 when the first driver portion 407 is pushed axially towards the second driver portion 412 (i.e., pushed in a proximal direction). In one arrangement, this may be achieved by pushing axially on a distal end of the spindle 414. This does not require any mechanism associated with removal of a cartridge holder. The mechanism is also designed such that the first and second driver portions 407, 412 and the spindle 414 remain locked together rotationally during dose setting as well as during dose administration.

An axial force on the spindle 414 causes the spindle 414 to rotate due to its threaded connection to the inner housing 408. This rotation and axial movement of the spindle 414 in turn causes the first driver portion 407 to move axially towards the second driver portion 412. This will eventually de-couple the coupling elements 450 between the first driver portion 407 and second driver portion 412. This can be seen from FIGS. 18 and 19.

This axial movement of the first driver portion 407 towards the second driver portion 412 results in certain advantages. For example, one advantage is that the metal spring 401 will compress and will therefore close the Gap A illustrated in FIGS. 21-23. This in turn prevents the clutch 405 from disengaging from the clicker 420 or from the number sleeve 406. The second driver 412 is prevented from rotation since it is splined to the clutch 405. The clicker 420 is splined to the housing 404. Therefore, when the Gap A is reduced or closed up, the second driver portion 412 cannot rotate relative to either the housing 404 or the number sleeve 406. As a consequence, the number sleeve 406 cannot rotate relative to the housing 404. If the number sleeve 406 is prevented from rotating then, as the spindle 414 is retracted back into the dose setting mechanism 400 and thereby re-set, there will be no risk of the number sleeve 406 being pushed out of the proximal side of the dose setting mechanism 400 as a result of a force being applied on the spindle 414.

Similarly, when the drug delivery device is being dispensed, the user applies an axial load to a dose button 416. The dose button 416 is axially coupled to the clutch 405 and this prevents relative axial movement. Therefore, the clutch 405 moves axially towards the cartridge end or the distal end of the dose setting mechanism 400. This movement disengages the clutch 405 from the number sleeve 406, allowing for relative rotation while closing up the Gap A.

As described above, this prevents the clutch 405 from rotating relative to the clicker 420 and hence relative to the housing 404. However, in this scenario, it also prevents the coupling between the first driver portion 410 and the second driver portion 412 from becoming disengaged. Therefore, any axial load on the spindle 414 only disengages the first and second driver portions 407, 412 when the dose button 416 is not axially loaded. This therefore does not happen during dispense.

With the dose setting mechanism 400, as a user dials a dose with the dose dial grip 402, the metal spring 401 is selected to be strong enough to maintain engagement of both clutched couplings: the clutched coupling between the clutch 405 and the number sleeve 406 and clutched coupling between the first driver portion 407 and second driver portion 412.

Figure 24:
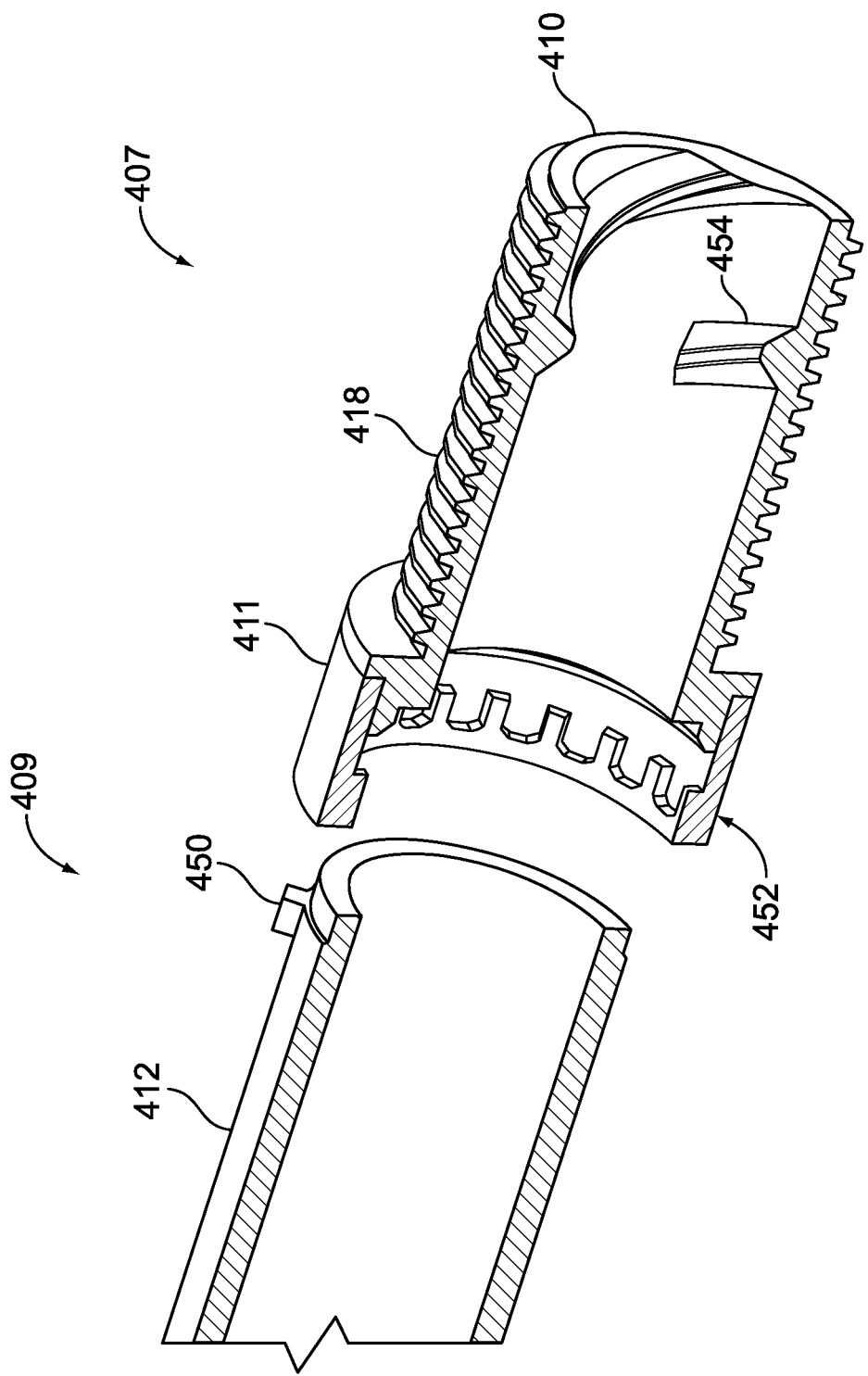
FIG. 24 illustrates a second arrangement of a driver comprising a first driver portion and a second driver portion.

FIG. 24 shows in detail a first arrangement of the first driver portion 407 and the second driver portion 412 illustrated in FIG. 21. As illustrated in FIG. 24, the second driver portion 412 is generally tubular in shape and comprises at least one drive dog 450 located at a distal end of the second driver portion 412. The first driver portion 407 also has a generally tubular shape and comprises a plurality of recesses 452 sized to engage with the drive dog 450 on the second driver portion 412. The construction of the drive dog and recesses allow disengagement with the drive dog 450 when the first and second driver portions are axially pushed together. This construction also creates a rotational coupling when these components are sprung apart. A dose limiter 418 is provided on first driver portion 407 and operates similarly to the dose limiter 128 illustrated in FIG. 3.

In this arrangement, the first driver portion 407 comprises a first portion 411 that is permanently clipped to a second portion 410. In this arrangement, the first portion 411 comprises the drive dogs 452 and the second component 410 includes the outer groove for the last dose nut as well as an internal groove 454. This internal groove 454 is used to connect to the spindle 414 and drives the spindle 414 during dose administration.

In the illustrated arrangement, the internal groove 454 comprises a part helical groove rather than a complete helical groove. One advantage of this arrangement is that it is generally easier to manufacture.

As may be seen from the arrangement illustrated in FIGS. 21-22 there is, in addition, certain feature enhancements over the dose setting mechanism 204 lustrated in FIGS. 16-18. These can be added independently of the ability to re-set the device to replace an empty cartridge with a new cartridge. These enhancements, therefore, are relevant to both a re-settable and non-re-settable dose setting mechanism.

One of the advantages of both arrangements illustrated but perhaps in particular in the arrangement illustrated in FIGS. 21-22 is that the dose setting mechanism 400 has a reduced number of components over other known dose setting mechanisms. In addition, apart from the metal coil spring 401, all of these components making up the dose setting mechanism 400 may be injection molded using inexpensive and unsophisticated tooling. As just one example, these components making up the dose setting mechanism 400 may be injection molded without the expense and sophistication of a rotating core.

Another advantage of a dose setting mechanism 400 comprising an inner housing 408 is that the dose setting mechanism 400 can be designed, with a slight modification, as a drug delivery device platform that is now capable of supporting both re-settable and non-resettable drug delivery devices. As just one example, to modify the re-settable dose setting mechanism 400 variant illustrated in FIGS. 21-22 into a non-resettable drug delivery device, the first driver portion 411 and 410 and the second driver portion 412 can be molded as one unitary part. This reduces the total number of drug delivery device components by two. Otherwise, the drug delivery device illustrated in FIGS. 21-22 could remain unchanged. In such a disposable device, the cartridge holder would be fixed to the housing or alternatively made as a single one piece body and cartridge holder.

The illustration in FIGS. 21-22 shows an inner housing 408 having a length "L" 430 generally similar in overall length to the dose setting mechanism 400. As will be described, providing the inner housing 408 with a length of "L" 430 has a number of advantages over other known dose setting mechanisms that do not utilize an inner body or an inner body having a length generally equal to that of the length of a dose setting mechanism.

The inner housing 408 comprises a groove 432 provided along an external surface 434 of the inner housing. A groove guide 436 provided on an inner surface 438 of the number sleeve 406 is rotatably engaged with this groove 432.

One advantage of this dose setting mechanism 400 utilizing the inner housing 408 is that the inner housing 408 can be made from an engineering plastic that minimizes friction relative to the number sleeve 406 groove guide 436 and the groove 432. For example, one such an engineering plastic could comprise Acetal. However, those of ordinary skill in the art will recognize that other comparable engineering plastics having a low coefficient of friction could also be used. Using such an engineering plastic enables the material for the outer housing 404 to be chosen for aesthetic or tactile reasons with no friction related requirements since the outer housing 404 does not engage any moving components during normal operation.

The inner housing 408 also enables the number sleeve 406 to be provided with a helical groove on an inner surface 438 of the number sleeve 406, rather than providing such a helical groove on an external surface 440 of the number sleeve 406. Providing such an internal groove results in a number of advantages. For example, this results in the advantage of providing more surface area along the outer surface 440 of number sleeve 406 so as to provide the scale arrangement 442. More number sleeve surface area may be used for drug or device identification purposes. Another advantage of providing the helical groove 436 on the inner surface 438 of the drive sleeve 406 is that this inner groove 436 is now protected from dirt ingress. In other words, it is more difficult for dirt to become logged in this inner groove interface than if the groove were provided along the outer surface 440 of the number sleeve 406. This feature is particularly important for a re-settable drug delivery device which will have to function over a much longer period of time compared to a non-resettable device.

The effective driving diameter (represented by 'D') of the grooved interface between the number sleeve 406 and the inner housing 408 is reduced compared to certain known drug delivery devices for the same outer body diameter. This improves efficiency and enables the drug delivery device to function with a lower pitch (represented by 'P') for this groove and groove guide connection. In other words, as the helix angle of the thread determines whether when pushed axially, the number sleeve will rotate or lock to the inner body wherein this helix angle is proportional to the ratio of P/D.

Figure 26:
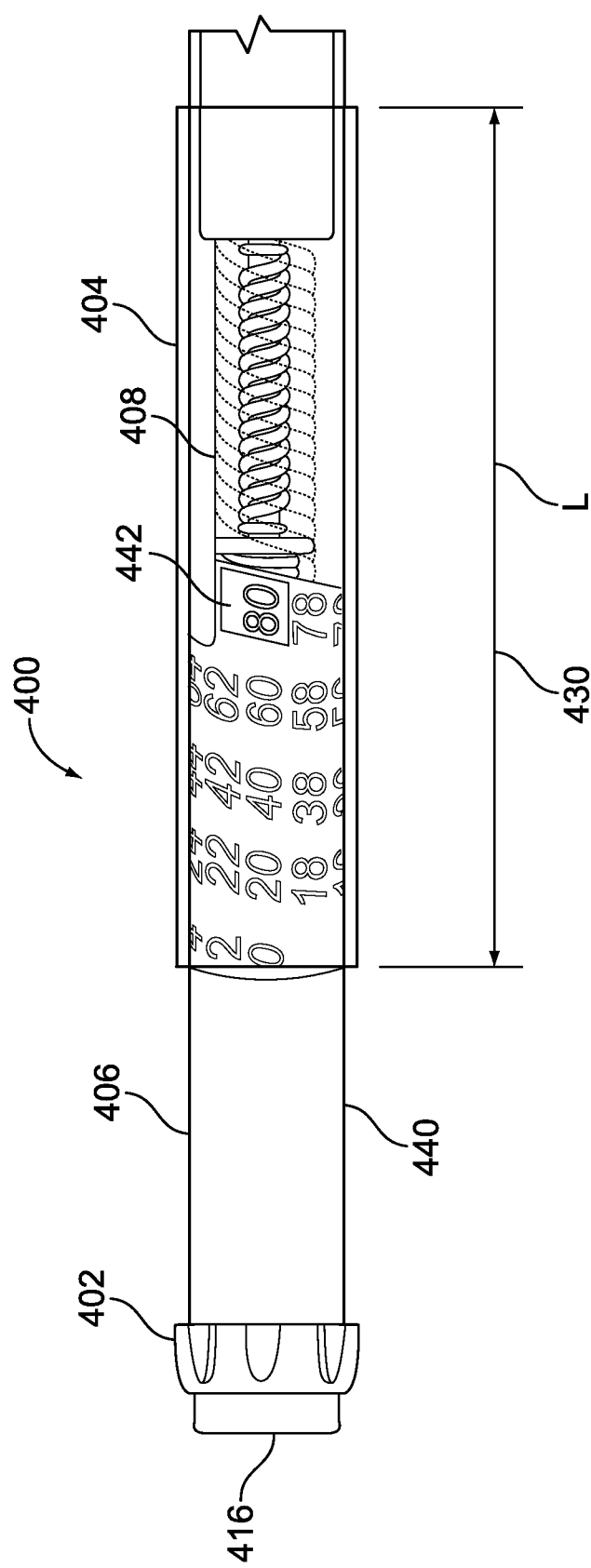
FIG. 26 illustrates the dose setting mechanism illustrated in FIG. 25 in which a user has set a dose.

The number sleeve 406 can be made the length of the mechanism "L" 430 rather than having to split this length into the space required for the number sleeve 406 and a space required for a clicker and a dose limiter. One advantage of this configuration is that it ensures a good axial engagement between the number sleeve 406 and the outer housing 404. This improves the functionality (and perceived quality) of the dose setting mechanism when a user uses the drug delivery device to dial out a maximum settable dose. FIG. 26 illustrates the dose setting mechanism 400 dialed out to a maximum settable dose of 80 International Units ("IU").

Another advantage is that it enables the scale arrangement 442 to be hidden within the outer housing 404 even when the number sleeve 406 is fully dialed out as may be seen from FIG. 26. However, the design does not limit the position of the window 14 but allows this window 14 to be positioned at near the dose dial grip 402 of the device. However, in arrangements illustrated in FIGS. 25 and 26, the scale arrangement 442 will only be visible by way of the window 414.

In addition, the driver 409 (whether made in two portions or just one unitary component) can be made with a plain internal through hole plus a thread form that can be molded with axially moving core pins. This avoids the disadvantage of a driver having an internal thread with more than one turn and therefore requires a core pin to be rotated out several turns during a de-molding process.

One potential disadvantage of utilizing a dose setting mechanism comprising the inner housing 408 is that the use of the inner housing 408 adds a component part to the overall dose setting mechanism 400. Consequently, this inner housing 408 will tend to increase the overall wall thickness that must be designed to fit between the clutch 405 and number sleeve 406. One way to work around this design issue, is to reduce the diameter of the clutch 405. This in turn can be achieved because the thread form between the driver 409 and the spindle 414 comprises a male internal feature 454 on the driver 409 and a female external groove form on the spindle 414 that is overlapping with (on a similar diameter with) the spindle groove form that interfaces with the groove along the inner surface of the inner housing 408 or body portion 516.

The overlapping of groove forms on the spindle 414 reduces the effective diameter of the thread interface with the driver 409. This also reduces the potential outer diameter of the driver 409 enabling the addition of the inner housing 408 without increasing the overall outer diameter of the dose setting mechanism 400. Another added benefit of the reduced effective diameter of the thread interface with the driver 409 is that it improves efficiency of the drug delivery device during dispense as explained above.

The window 444 through which the scale arrangement 442 may be viewed can either be just an aperture in the outer housing 404 or can include a clear lens or window designed to magnify the scale arrangement (i.e., printed or laser marked dose numbers) along a portion of the outer surface 440 on the number sleeve 406.

The connection of a cartridge holder into the outer housing 404 can be achieved using either a screw or bayonet type connection. Alternatively, any similarly robust design used in drug delivery devices requiring a largely cylindrical part to be removed and then reattached could also be used.

As described above, the first arrangement of the drug delivery device illustrated in FIGS. 16-20 and the second arrangement of the drug delivery device illustrated in FIGS. 21-24 comprise a spindle having two helical grooves. Specifically, this spindle has two opposite handed overlapping groove forms that preferably extend over at least a majority of a length of the spindle. Each groove form is effectively continuous over a number of turns. In one preferred arrangement, each groove of the spindle engages either a non-continuous helical groove form on a body portion or a driver. Preferably, either or both a non-continuous thread form on a body and a driver consists of less than one complete turn of thread.

The spindle and driver configuration of these preferred arrangements can be used in a drug delivery device, such as an injection pen type device. With certain injection pen type devices, robust tool design is one very important issue to reducing the overall manufacturing costs, and also providing for good dose accuracy. As such, the spindle and driver design of Applicants application may also be used in various types of drug delivery devices, such as reusable or disposable pen type injection devices. The lead of both groove forms on the spindle assist to control the accuracy of the dose dispensed. This is in contrast to certain prior art devices where the dose accuracy is dependent on both the groove form on the spindle and the groove form on the driver.

Figure 27:
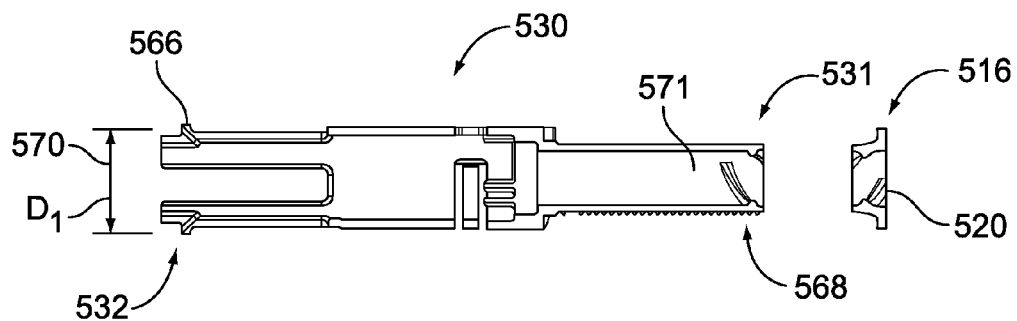
FIG. 27 illustrates a driver that may be used with a dose setting mechanism of the drug delivery device illustrated in FIG. 14-15.
Figure 28:
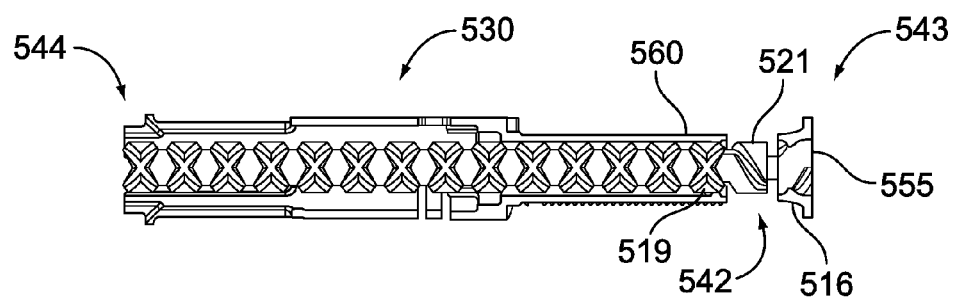
FIG. 28 illustrates a spindle coupled to the driver illustrated in FIG. 27.

One exemplary arrangement of Applicants' spindle and driver arrangement is illustrated in FIGS. 27 and 28. FIG. 27 illustrates a driver 530 and a body portion 516 that may be used in a drug delivery device, such as the drug delivery device illustrated in FIGS. 14-26. In FIG. 27, the driver 530 is illustrated as a single component. However, similar to the driver 230 illustrated in FIGS. 15-18, driver 530 may alternatively comprise a first driver portion and a second driver portion.

As illustrated in FIGS. 27-28, the driver 530 comprises a generally tubular member extending between a distal end 531 and a proximal end 532. The driver 530 has a first groove form 568 at the distal end. Preferably, the first groove form 568 comprises a partial male groove form that engages one of the helical grooves along the surface 560 of the spindle 542.

Also illustrated in FIG. 27 is a housing inset 516. Housing insert 516 comprises a groove portion 520 that engages a helical groove provided on spindle 542.

In one exemplary arrangement of the design of a spindle and driver as illustrated in FIGS. 27-28, the driver 530 comprises a male groove form 568 located at a distal end 531 of the driver. This male groove form 568 resides on an internal surface 571 of the driver 530 and preferably comprises a groove form of less than one turn. This groove form engages a first groove 519 provided along a surface of the spindle 542. In a preferred arrangement, this first spindle groove 519 is effectively continuous not just for a portion of the spindle surface 560 but for a majority of the length of the spindle as illustrated. In this instance, if the driver 530 is rotated during dose setting relative to the spindle 542 (as discussed above), then the axial displacement of the spindle 542 relative to the housing during dose dispense will be dependent on the pitch of the helical grooves 519 and 521 on the spindle 542 and will not be dependent on the pitch of the male groove form 568 on the driver. This is in contrast to what occurs in the prior art drug delivery device illustrated in FIGS. 1-13 and discussed above.

FIG. 28 illustrates the spindle 542 engaged to the driver 530 and insert 516. In one arrangement, the two pitches of the spindle are certain discrete proportions of each other such as the same pitch 1:1 or ratios such as 2:1, 1.66:1. However, if the grooves are not overlapping as with prior art there are no limitations to the ratios of the two pitches and the spindle can equally be molded in an open and shut tool construction. In contrast to the spindle of the prior art drug delivery device illustrated in FIGS. 1-13 where molding of the driver 30 requires a core pin that must to be rotated out of the mold, the driver 530 illustrated in FIG. 27, (because it has less that one turn of groove), can be advantageously molded using two cores, neither of which rotate during mold release. For example, during the molding process of this driver 530, these two cores can be merely moved axially during a part ejection step. Consequently, the use of two such molds can significantly reduce the cost, the maintenance, and the cycle time of the molding tool used to mold this preferred driver configuration.

The preferred design of this spindle 542 having two overlapping grooves may be embodied in several ways. As mentioned above, one key advantage of such a spindle construction is that the spindle 542 and driver 530 arrangement may be molded by way of a less complex method. Moreover, the advance of the spindle 542 in the distal direction when the driver 530 is advanced during dose administration is dependent on the magnitude of the pitch of the first and the second groove forms 519, 521 of the spindle 542. Therefore, the dose dispensed is linked only to the dimensions of the spindle and no other component. This spindle could therefore be made from a material that has a very low or consistent shrinkage to improve dose accuracy.

Additionally however as the helical groove form 568 of the driver 530 is a male form and radially protrudes inwardly as illustrated in FIG. 27, rather than a female form that cuts radially outwards into a tubular body of the driver, as the prior art driver illustrated in FIGS. 1-12. With such a male form as illustrated in FIG. 27, the outer diameter D1 570 of the driver 530 can be reduced over other prior art type devices. One advantage of reducing the outer diameter D1 570 of the driver 530 is that this reduced diameter enables the overall diameter of the drug delivery device to be more compact. One advantage of a more compact drug delivery device is that it brings the visual appearance of the drug delivery device closer to that of typical writing pens. As just one example, the outer diameter D2 of the drug delivery device 201 illustrated in FIG. 14 can be made smaller than the outer diameter D3 of the drug delivery device illustrated in FIG. 1.

Furthermore, if the driver 530 engages the spindle groove 519 only at the distal end 531 of the driver (in contrast to where the driver 30 engages the spindle helix over a larger portion of the spindle as illustrated in the spindle and driver arrangement of FIGS. 1-13), the spindle 542 can extend in a proximal direction beyond the end of the driver 530. One benefit of such a driver and spindle arrangement is that it enables the overall length of the drug delivery device to be reduced. As just one example of this benefit is that the overall length L2 11 of the prior art drug delivery device illustrated in FIGS. 1-13 can be reduced to a shorter overall length of L3 120 of the drug delivery device 201 illustrated in FIG. 14.

In the driver and spindle arrangement illustrated in FIGS. 27-28, this arrangement may be utilized in a disposable or non-resettable drug delivery device. In an alternative arrangement, the driver may be split into multiple portions (e.g., two or more) that are separated axially. In such an arrangement, a first driver portion (closest to the cartridge) would engage with the spindle helix and in engagement with a dose limiting mechanism, similar to the dose mechanism 238 illustrated in FIG. 16. The short non-continuous thread form 568 on the first driver portion and continuous groove form 519 on the spindle enables a design for a drug delivery device where just this first driver portion rotates as the spindle is pushed back into the second driver portion. There is no need for the two driver portions to be concentrically disposed. Such a configuration would add to the overall outer diameter of the drug delivery device.

Another advantage of using the spindle 542 having two overlapping groove forms 519, 521 is that such an arrangement creates radial space within the drug delivery device. In one arrangement, this radial space may be used to introduce an inner body component within the drug delivery device, such as the inner body 208 illustrated in FIG. 21 and as described in detail above.

However as can be seen from the spindle 542 illustrated in FIG. 28 it is advantageous to have a pitch of thread interface with the driver 530 to be a specific multiple of a pitch of a groove form 520 with the spindle 542. One reason for this is that it can ensure that both groove forms 519, 521 cross over one another at certain defined angular planes that are rotated around the axis of the spindle 542.

As just one example, in the case of the spindle illustrated in FIG. 28, the pitch of the driver 530 to spindle groove form 519 is equal to that of the spindle groove 521 to housing portion 516 groove form. One advantage of this configuration is that it ensures that with two equally spaced starts for each groove form, the groove forms cross over one another every 90°. With the typical groove pitches used, this enables the spindle 542 to be molded with a two slide open and shut tool construction. Of course other ratios may also be used. However, as one of skill in the art will recognize, there are a certain limited number of range of ratios that will enable the spindle to be molded easily with injection mould tooling. Alternatively if the ratio is 2:1, the grooves cross over every 60° and with carefully designed thread forms this ratio can still be molded with an open and shut mold tool construction.

In one of Applicants preferred drug delivery device spindle and driver arrangements, the ratio of these two spindle groove form pitches define a certain mechanical advantage of the drug delivery device. In one arrangement, this mechanical advantage may be defined by the formula (A+B)/A. In this formula, A may define the groove pitch between the spindle 519 and housing portion 516 and B may define the groove pitch between the spindle helical groove 521 and the driver groove portion 568. As such, the mechanical advantage in turn defines a maximum dial out distance for a given maximum dose value. As just one example, a mechanical advantage of three to one ("3:1") and a maximum dose of 80 International Units ("IU") would result in a dial out distance of 33.12 millimeters (mm) for a nominal cartridge internal diameter of 9.6 mm.

Figure 25:
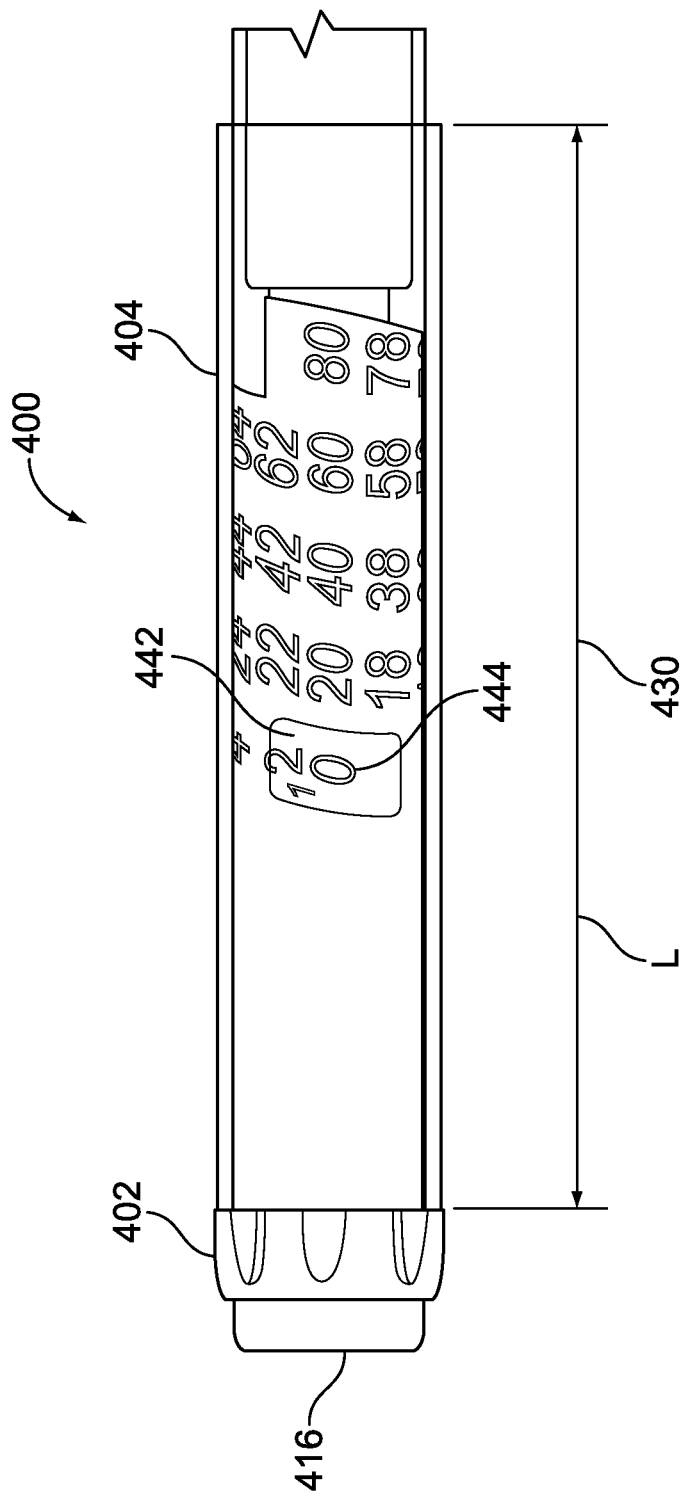
FIG. 25 illustrates the dose setting mechanism illustrated in either FIGS. 2-5 or FIGS. 6-8.

This dial out distance can affect an overall length of a drug delivery device. In particular, significantly affects the length of the drug delivery device if the numbers on the number sleeve are to remain hidden inside the housing when the maximum dose is dialed as illustrated in FIGS. 25-26.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A dose setting mechanism for use with a drug delivery device, said dose setting mechanism comprising:
   a housing insert comprising a helical groove form;
   a spindle for driving a bung of a cartridge, said spindle comprising:
      a generally circular shaft having an outer surface;
      a first helical groove provided along a first portion of said outer surface of said generally circular shaft, said first helical groove having a first pitch; and
      a second helical groove provided along a second portion of said outer surface of said generally circular shaft, said second helical groove overlapping said first helical groove, said second helical groove having a second pitch, and said second helical groove engaging the helical groove form of the housing insert; and
   a driver for driving said spindle, said driver comprising a helical groove form that engages said first helical groove provided along said first portion of said outer surface of said generally circular shaft of said spindle,
   wherein a longitudinal axial movement of the driver causes the spindle to rotate, and
   wherein the driver is prevented from rotating with respect to a drug delivery device housing during dispensing a dose.

2. The invention of claim 1 wherein said first helical groove comprises said first pitch of a first hand; and said second helical groove comprising said second pitch of an opposite hand to said first hand of said first helical groove.

3. The invention of claim 1 wherein said first pitch of said first helical groove is equivalent to said second pitch of said second helical groove.

4. The invention of claim 1 wherein said second helical groove provided along said second portion of said outer surface of said generally circular shaft overlaps substantially all of said first helical groove.

5. The invention of claim 1 wherein said first helical groove provided along said outer surface of said generally circular shaft comprises a first helical female groove.

6. The invention of claim 1 wherein said second helical groove provided along said outer surface of said generally circular shaft and overlapping at least a portion of said first helical groove comprises a second helical female groove.

7. The invention of claim 1 wherein said helical groove form of the driver comprises a helical groove of less than one turn.

8. The invention of claim 1 wherein said first helical groove extends along said outer surface of said generally circular shaft from about said distal end of said spindle to about said proximal end of said spindle.

9. The invention of claim 1 wherein said second helical groove extends along said outer surface of said generally circular shaft from about said distal end of said spindle to about said proximal end of said spindle.

10. The invention of claim 1 wherein said helical groove form of said housing insert comprises a partial groove form.

11. The invention of claim 1 wherein said helical groove form of said housing insert comprises a less than one complete turn of said groove.

12. The invention of claim 1 wherein said cartridge comprises a removable cartridge of a drug delivery device.

13. The invention of claim 1 wherein said cartridge comprises a non-removable cartridge of a drug delivery device.

14. The invention of claim 1 wherein said first pitch of said first helical groove provided along said first portion of said outer surface has a first diameter and said second pitch of said second helical groove provided along said second portion of said outer surface has a second diameter.

15. The invention of claim 14 wherein said first diameter is generally equal to said second diameter.

16. The invention of claim 1, further comprising:
   a rotating sleeve in rotatable engagement with respect to said drug delivery device housing;
   wherein the driver is releasably coupled to said rotating sleeve such that when a user sets a dose by rotating said rotating sleeve, said driver also rotates.

17. The invention of claim 16 where said dose setting mechanism comprises a resettable dose setting mechanism.

18. The invention of claim 16 wherein said driver comprises a first component and a second component, said first and said second component being operatively coupled together so that they rotate together when said user sets said dose.

19. The invention of claim 16 wherein said dose setting mechanism comprises a non-resettable dose setting mechanism.

20. The invention of claim 17 wherein when said user resets said dose setting mechanism, a first component of said driver is decoupled from a second component of said driver and said first component can rotate back to an original position.

21. The invention of claim 20 wherein when said user resets said dose setting mechanism and said first component rotates back to said original position, a dose limiting device returns to an initial position.

22. The invention of claim 20 further comprising a cartridge holder releasably coupled to said dose setting mechanism.

23. The invention of claim 20 further comprising a cartridge holder releasably coupled to said dose setting mechanism by way of a bayonet coupling.

24. The invention of claim 20 further comprising a cartridge holder comprising a removable cartridge.

* * * * *